United States Patent
Ebi et al.

(10) Patent No.: US 9,329,111 B2
(45) Date of Patent: May 3, 2016

(54) SAMPLE PREPARATION APPARATUS

(75) Inventors: Ryuichiro Ebi, Osaka (JP); Koki Tajima, Kobe (JP); Tokihiro Kosaka, Kakogawa (JP)

(73) Assignee: SYSMEX CORPORATION, Kobe-shi (JP)

( * ) Notice: Subject to any disclaimer, the term of this patent is extended or adjusted under 35 U.S.C. 154(b) by 4 days.

(21) Appl. No.: 13/007,331

(22) Filed: Jan. 14, 2011

(65) Prior Publication Data

US 2011/0176934 A1 Jul. 21, 2011

(30) Foreign Application Priority Data

Jan. 15, 2010 (JP) ................................. 2010-007168
Mar. 23, 2010 (JP) ................................. 2010-066405

(51) Int. Cl.
*G01N 9/30* (2006.01)
*B01D 45/00* (2006.01)
*B01D 35/00* (2006.01)
*G01N 1/40* (2006.01)
*G01N 15/14* (2006.01)
*G01N 35/00* (2006.01)

(52) U.S. Cl.
CPC .............. *G01N 1/4077* (2013.01); *G01N 15/14* (2013.01); *G01N 2001/4088* (2013.01); *G01N 2035/00495* (2013.01)

(58) Field of Classification Search
CPC ............ G01N 1/34; G01N 2001/4088; G01N 15/147; G01N 15/1475; G01N 1/4077; G01N 2015/1006; G01N 2015/1493; G01N 35/1095; G01N 15/1459; G01N 15/14; G01N 15/1429; G01N 15/1434; G01N 1/38; G01N 1/40; G01N 2035/00495; G01N 33/4833; G01N 33/57496; G01N 35/00613; G01N 35/02; B01L 2200/0647; B01L 2200/14; B01L 2200/143; B01L 2300/0681; B01L 2300/0832; B01L 2300/0858; B01L 3/502; B01L 3/52

USPC ............ 422/72, 50, 415, 68.1, 500–504, 506, 422/513, 527, 533, 534, 209, 258, 259, 269, 422/271; 702/127, 142, 145

See application file for complete search history.

(56) References Cited

U.S. PATENT DOCUMENTS

| | | | |
|---|---|---|---|
| 5,672,481 A * | 9/1997 | Minshall et al. | ............. 435/7.21 |
| 2011/0014685 A1 | 1/2011 | Fukuda et al. | |
| 2011/0036150 A1 | 2/2011 | Sakai | |

FOREIGN PATENT DOCUMENTS

| | | |
|---|---|---|
| EP | 2 261 632 A1 | 12/2010 |
| JP | 63-12936 A | 1/1988 |
| JP | 2007-54817 A | 3/2007 |
| WO | 2009/123000 A1 | 10/2009 |
| WO | 2009/131185 A1 | 10/2009 |

* cited by examiner

*Primary Examiner* — Dean Kwak
(74) *Attorney, Agent, or Firm* — Mots Law, PLLC

(57) ABSTRACT

A sample preparation apparatus comprising: a filter which separates predetermined cells from a liquid sample containing a plurality types of cells; a rotor which includes a magnetic body and detaches the predetermined cells attached to the filter by rotation; a driving unit which rotates the rotor using a magnetic force; and a rotation information acquiring unit which acquires a rotation information of the rotor when the driving unit rotates the rotor. A method and a computer program product are also disclosed.

19 Claims, 20 Drawing Sheets

SAMPLE PREPARATION APPARATUS

FIELD OF THE INVENTION

The present invention relates to a sample preparation apparatus, a sample preparation method, and a computer program.

BACKGROUND

As a cell analyzer for analyzing cells contained in a biological sample collected from a living body, a cell analyzer for measuring epithelial cells of the uterine cervix contained a sample collected from the uterine cervix of a subject by a flow cytometer and screening cancer and atypical cells is conventionally known (e.g. European Patent publication No. EP2261632).

In addition to the epithelial cells to be analyzed, contaminants such as red blood cells and white blood cells are also contained in the sample collected from the uterine cervix of the subject. When such a sample is measured as it is, the presence of the contaminants affects the measured results, resulting in being unable to perform an accurate screening. Therefore, it is necessary to discriminate the epithelial cells to be analyzed from the contaminants.

In the apparatus described in European Patent publication No. EP2261632, the epithelial cells are discriminated from the contaminants by trapping the epithelial cells to be analyzed in a filter, aspirating the contaminants passed the filter, and discharging them using the fact that the size of the epithelial cells to be analyzed is larger than that of the contaminants.

In order to prepare a measurement sample containing the epithelial cells, it is necessary to detach the epithelial cells trapped in the filter from the filter and recover them. The detachment is performed by applying a shearing force generated by rotating a rotor arranged adjacent to the filtration surface of the filter to the surface of the filter.

In the cell analyzer described in European Patent publication No. EP2261632, when detaching the epithelial cells attached to the filter by the rotor, the rotor may not rotate or the rotation may not be sufficient due to reasons that the epithelial cells are adhered to the rotor or the wall surface around the rotor. When the rotation of the rotor is not sufficient, the epithelial cells to be measured cannot be sufficiently taken.

SUMMARY

The scope of the present invention is defined solely by the appended claims, and is not affected to any degree by the statements within this summary.

A first aspect of the present invention is a sample preparation apparatus comprising: a filter which separates predetermined cells from a liquid sample containing a plurality types of cells; a rotor which includes a magnetic body and detaches the predetermined cells attached to the filter by rotation; a driving unit which rotates the rotor using a magnetic force; and a rotation information acquiring unit which acquires a rotation information of the rotor when the driving unit rotates the rotor.

A second aspect of the present invention is a sample preparation method, comprising: acquiring the rotation information of the rotor, wherein the rotor detaches predetermined cells attached to the filter which separates the predetermined cells from the liquid sample containing the plurality types of cells and which includes the magnetic body; and controlling the driving unit which rotates the rotor using the magnetic force based on the acquired rotation information of the rotor.

A third aspect of the present invention is a computer program product, comprising: a computer readable medium; and instructions, on the computer readable medium, adapted to enable a general purpose computer to perform operations, comprising: acquiring the rotation information of the rotor, wherein the rotor detaches predetermined cells attached to the filter which separates the predetermined cells from the liquid sample containing the plurality types of cells and which includes the magnetic body; and controlling the driving unit which rotates the rotor using the magnetic force based on the acquired rotation information of the rotor.

DETAILED DESCRIPTION OF THE EMBODIMENT

The embodiments of the sample preparation apparatus of the present invention will be described in detail below with reference to the accompanying drawings.

The sample preparation apparatus of the present invention can be used in the cell analyzer which analyzes cells collected from patients. First, the cell analyzer will be described.

[Overall Configuration of the Cell Analyzer]

Figure 1:
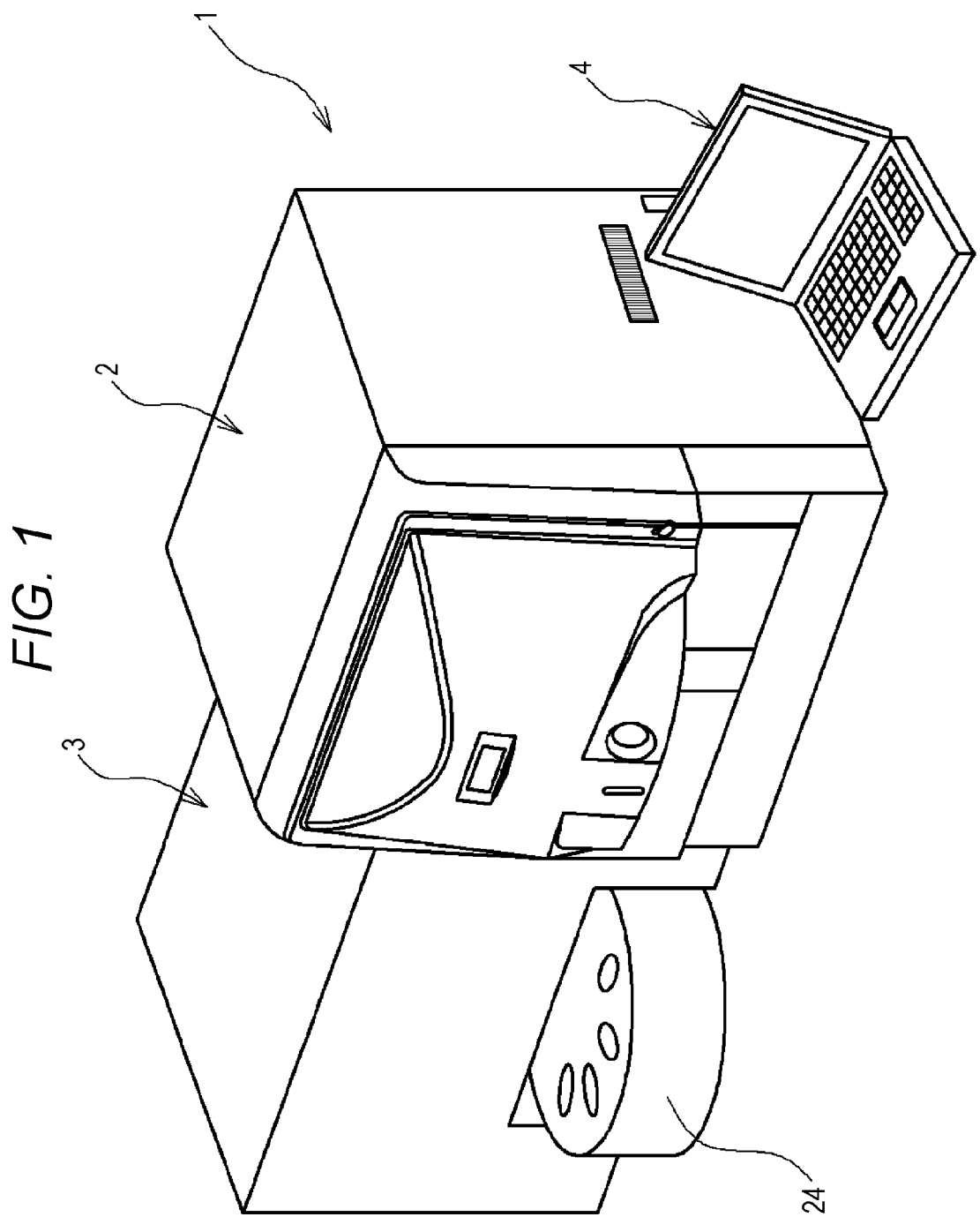
FIG. 1 is a perspective view of a cell analyzer having a sample preparation apparatus according to one embodiment of the present invention.

FIG. 1 is a perspective view of a cell analyzer 1 having a sample preparation apparatus according to one embodiment of the present invention.

The cell analyzer 1 is used for determining whether or not cancer cells are contained in the cells by flowing a measurement sample containing the cells collected from the patients into a flow cell, irradiating the measurement sample flowing through the flow cell with a laser beam, detecting light from the measurement sample (scattered light or fluorescence (e.g. forward scattered light and lateral fluorescence)), and analyzing the light signals thereof.

More specifically, the cell analyzer 1 of the present embodiment is intended to analyze epithelial cells of the uterine cervix and used for screening uterine cervix carcinoma.

As shown in FIG. 1, the cell analyzer 1 includes a measurement apparatus 2 which performs optical measurement with a laser beam on the measurement sample, a sample preparation apparatus 3 which produces the measurement sample to be supplied to the measurement apparatus 2 by subjecting a biological sample collected from a subject to pretreatments such as cleaning and staining, and a data processing apparatus 4 which analyzes the measured results in the measurement apparatus 2.

A main constituent element of the cell analyzer 1 will be sequentially described.

[Internal Configuration of the Measurement Apparatus]

Figure 2:
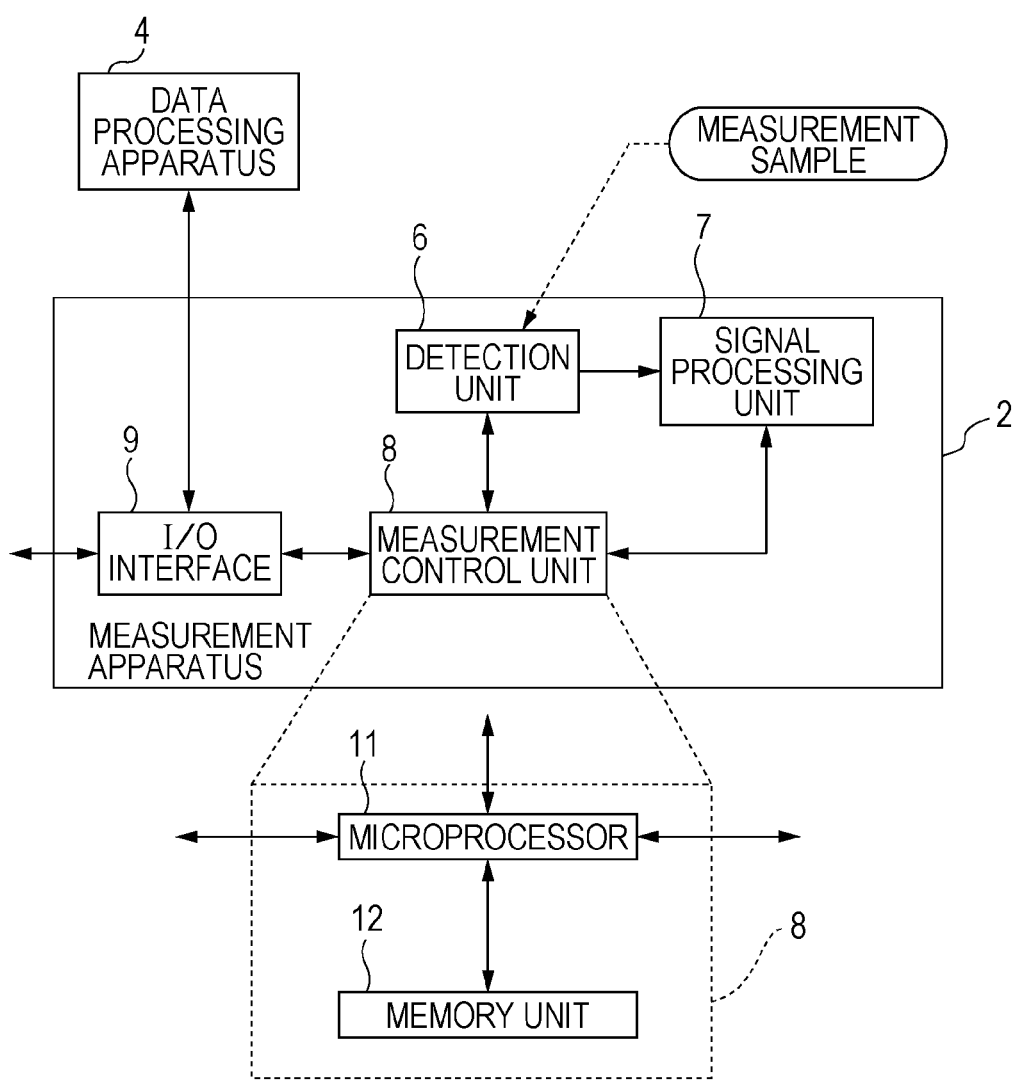
FIG. 2 is a block diagram showing an internal configuration of a measurement apparatus.

FIG. 2 is a block diagram showing an internal configuration of a measurement apparatus 2.

As shown in FIG. 2, the measurement apparatus 2 includes a detection unit 6, a signal processing unit 7, a measurement control unit 8, and an I/O interface 9.

Figure 5:
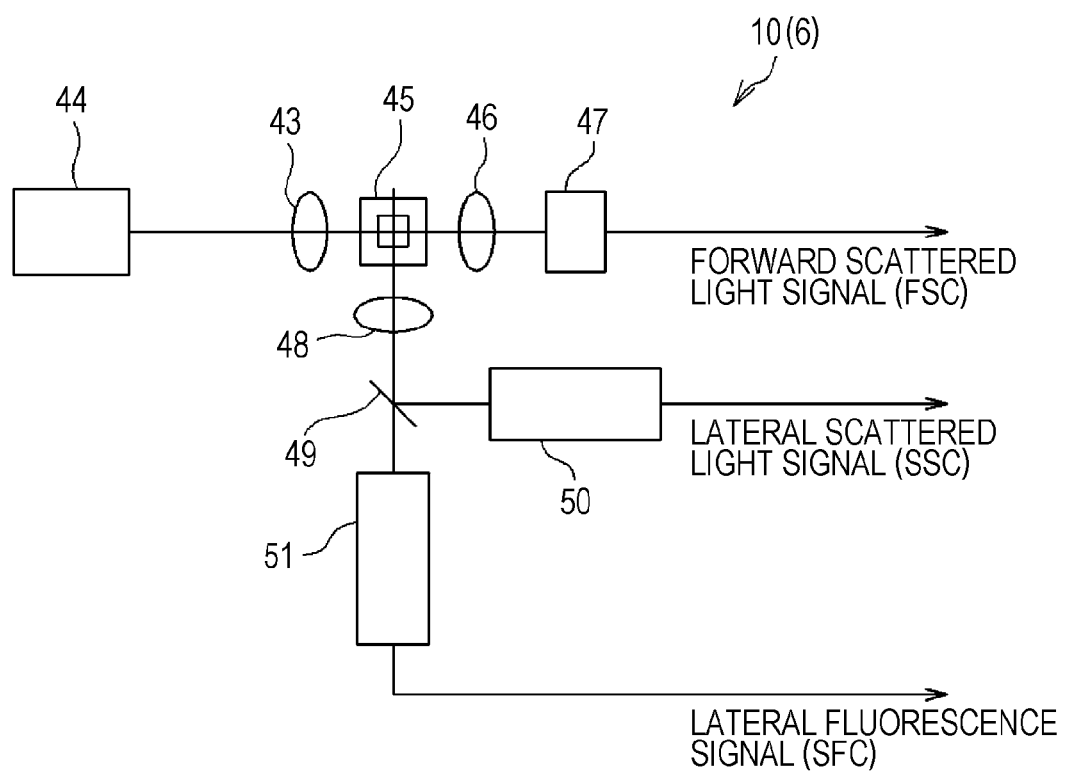
FIG. 5 is a functional block diagram of a flow cytometer which includes a detection unit.
Figure 6:
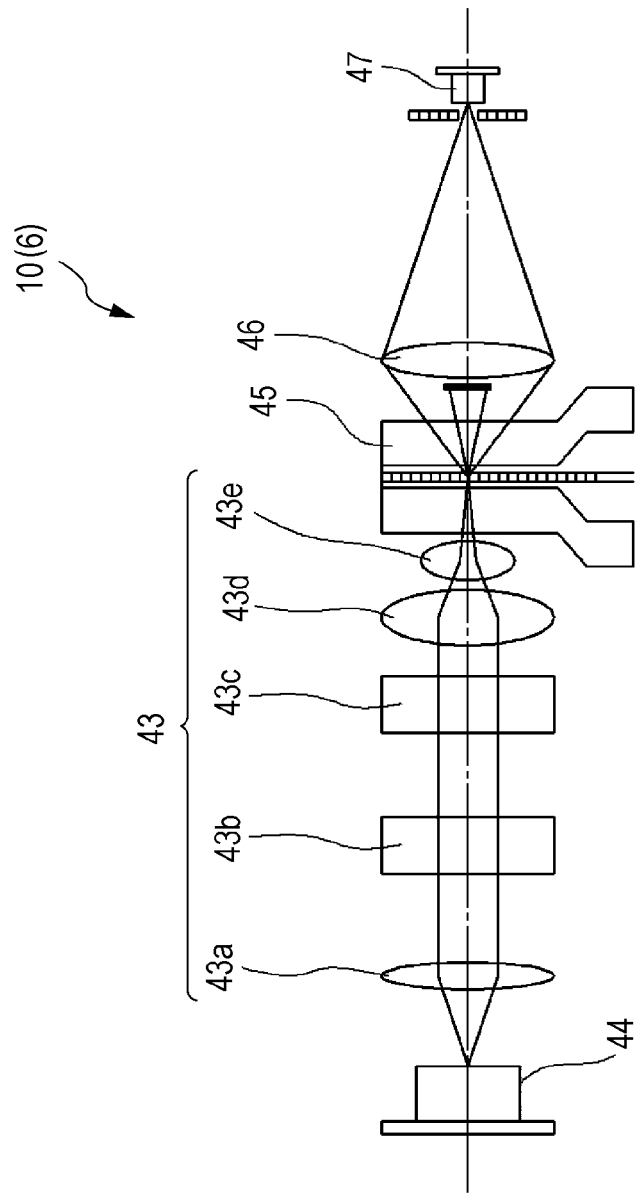
FIG. 6 is a side view showing an optical system of the flow cytometer.

Among them, the detection unit 6 detects cells to be measured and the number and size of nuclei in the cells from the measurement sample and a flow cytometer 10 shown in FIGS. 5 and 6 is employed in the present embodiment.

The signal processing unit 7 includes a signal processing circuit which performs a required signal process on an output signal from the detection unit 6. The measurement control unit 8 includes a microprocessor 11 and a memory unit 12 and the memory unit 12 includes a ROM, a RAM, and the like.

Control programs which perform operation control of the detection unit 6 or the signal processing unit 7 as well as data required for executing the control programs are stored in the ROM of the memory unit 12. The microprocessor 11 is capable of executing the control programs loaded in the RAM or directly executing the control programs in the ROM.

The microprocessor 11 of the measurement control unit 8 is connected to the data processing apparatus 4 and a microprocessor 19 of a preparation control unit 16 to be described later through the I/O interface 9. Thus, the data processing apparatus 4 can transmit and receive data processed by the microprocessor itself or data required for the microprocessor's own process with the microprocessor 19 of the preparation control unit 16.

[Internal Configuration of the Sample Preparation Apparatus]

Figure 3:
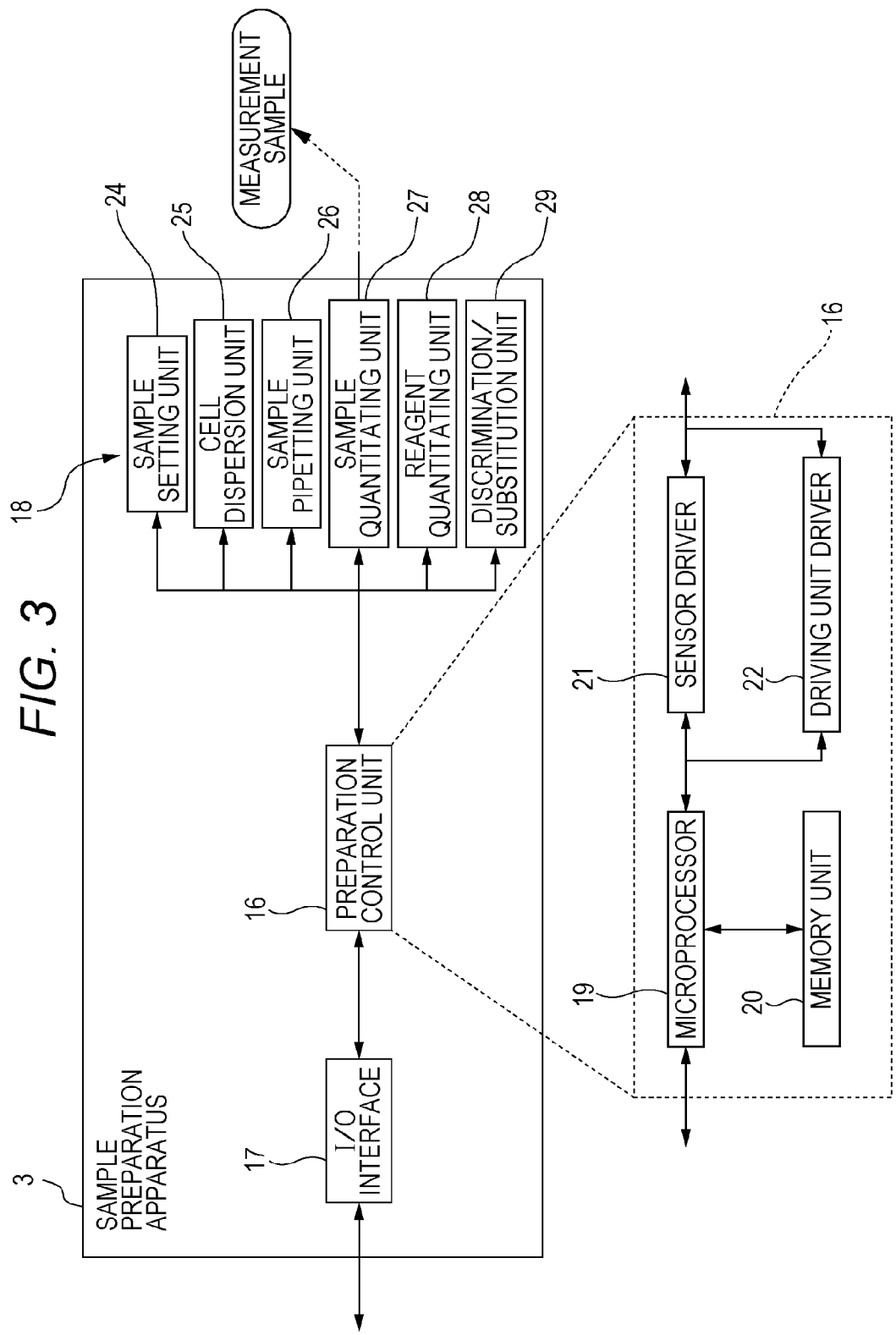
FIG. 3 is a block diagram showing an internal configuration of the sample preparation apparatus.

FIG. 3 is a block diagram showing an internal configuration of the sample preparation apparatus 3.

As shown in FIG. 3, the sample preparation apparatus 3 includes the preparation control unit 16, an I/O interface 17, and a preparation device unit 18 which automatically adjusts components of the biological sample.

The preparation control unit 16 includes the microprocessor 19, a memory unit 20, a sensor driver 21, and a driving unit driver 22. The memory unit 20 includes a ROM, a RAM, and the like.

The preparation device unit 18 of the present embodiment is configured by a sample setting unit 24, a cell dispersion unit 25, a sample pipetting unit 26, a sample quantitating unit 27, a reagent quantitating unit 28, and a discrimination/substitution unit 29.

A plurality of biological sample containers 53 and measurement sample containers 54 which hold biological samples collected from the patients and a preservative solution containing methanol as a main ingredient (see FIG. 7) are set in the sample setting unit 24 among them. The cell dispersion unit 25 forcedly disperses cells contained in the sample by stirring a mixed solution of the biological samples and the preservative solution in the biological sample containers 53.

The sample pipetting unit 26 introduces the mixed solution of the biological samples containing the dispersed cells and the preservative solution retrieved from the biological sample containers 53 into the fluid circuit of the preparation device unit 18, and retrieves a prepared liquid sample returned to the measurement sample containers 54 from the measurement sample containers 54. The sample quantitating unit 27 quantifies the mixed solution of the biological samples and the preservative solution to be supplied to the fluid circuit. The reagent quantitating unit 28 quantifies a reagent such as a stain solution to be added to the biological samples.

The discrimination/substitution unit 29 substitutes the preservative solution with a diluted solution and discriminates cells to be measured from the other cells (red blood cells, white blood cells, etc.) and bacteria, and the like. The discrimination/substitution unit 29 prepares a liquid sample in which the concentration of the cells to be measured is increased from the liquid sample containing the discriminated and substituted cells to be measured. The configuration of the fluid circuit of the preparation device unit 18 having respective units 24 to 29 (FIGS. 7 to 8) will be described later.

Control programs which perform operation control of the sensor driver 21 and the driving unit driver 22 as well as data required for executing the control programs are stored in the ROM of the memory unit 20. The microprocessor 19 is capable of executing the control programs loaded in the RAM or directly executing the control programs in the ROM.

The microprocessor 19 of the preparation control unit 16 is connected to the microprocessor 11 of the measurement control unit 8 through the I/O interface 17. Thus, the microprocessor 19 can transmit and receive data processed by the microprocessor itself or data required for the microprocessor's own process with the microprocessor 11 of the measurement control unit 8.

The microprocessor 19 of the preparation control unit 16 is connected to sensors of respective units 24 to 29 in the preparation device unit 18 and a driving motor configured by the driving unit through the sensor driver 21 and a driving unit driver 22, executes the control programs based on detection signals from the sensors, and controls the operation of the driving unit.

[Internal Configuration of the Data Processing Unit]

Figure 4:
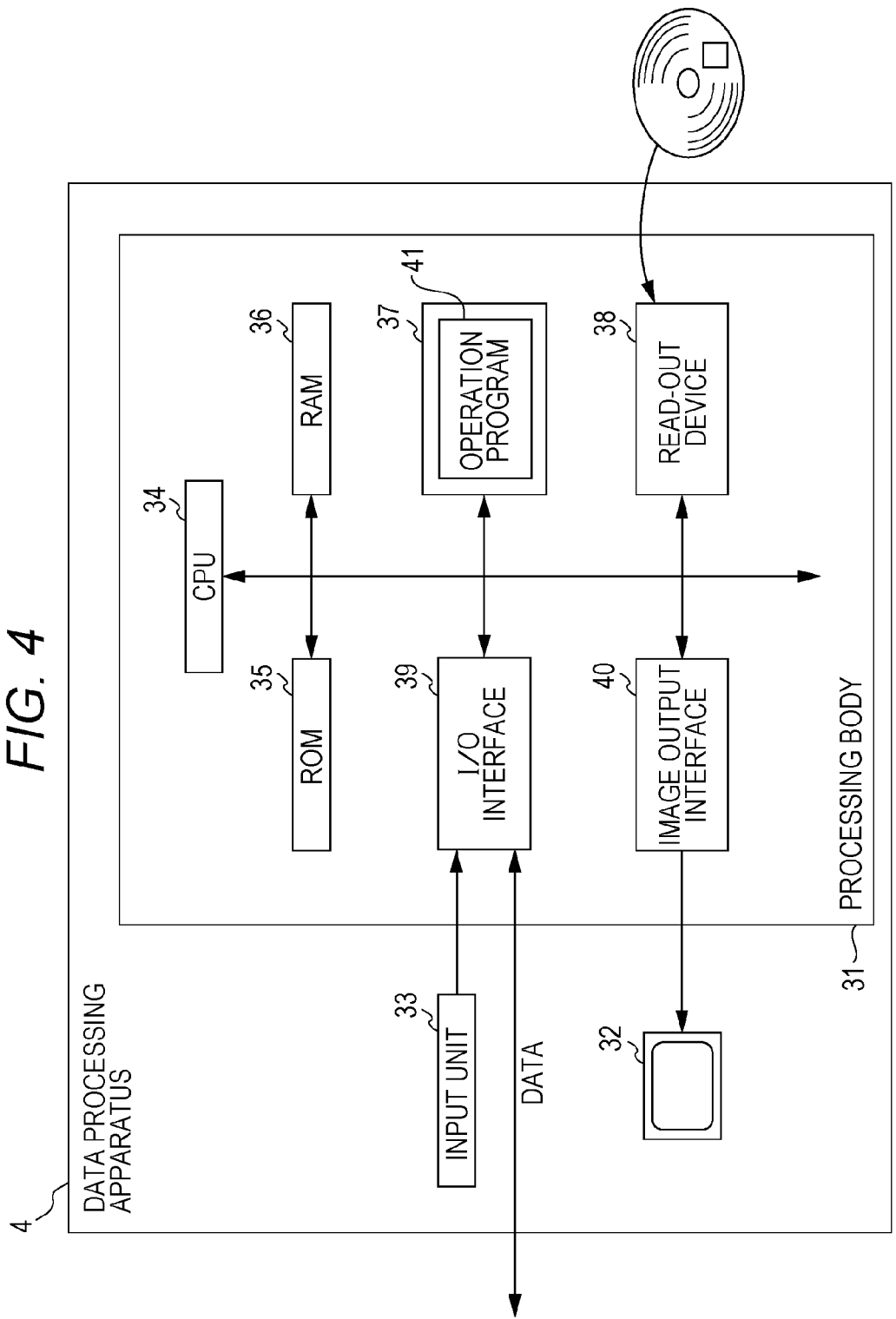
FIG. 4 is a block diagram showing an internal configuration of a data processing apparatus.

FIG. 4 is a block diagram showing an internal configuration of a data processing apparatus 4.

As shown in FIG. 4, the data processing apparatus 4 of the present embodiment is configured by a personal computer, for example, a notebook PC (a desktop type PC may be used.) and mainly includes a processing body 31, a display 32, and an input unit 33.

The processing body 31 includes a CPU 34, a ROM 35, a RAM 36, a hard disk 37, a read-out device 38, an I/O interface 39, and an image output interface 40. Each of these units is communicably connected by an internal bus.

The CPU 34 is capable of executing the computer programs stored in the ROM 35 and the computer programs loaded in the RAM 36.

The ROM 35 is configured by a mask ROM, a PROM, an EPROM, an EEPROM, and the like. The computer programs to be executed by CPU 34 and data to be used for the computer programs are stored in the ROM 35.

The RAM 36 is configured by a SRAM, a DRAM, or the like, and is used to read out various computer programs recorded on the ROM 35 and the hard disk 37 or is used as a work region of the CPU 34 when executing the computer programs.

Various computer programs to be executed by the CPU 34 such as operating system and application program, as well as data used in executing the programs are installed in the hard disk 37.

An operating system providing a graphical user interface environment such as Windows (registered trademark) manufactured and sold by US Microsoft Co. is installed in the hard disc 37.

Further, an operation program 41 which performs transmission of operation instructions to the measurement control unit 8 and the preparation control unit 16, processes of receiving and analyzing measured results performed by the measurement apparatus 2, and display of processed analysis results is installed in the hard disc 37. The operation program 41 is assumed to operate on the operating system.

The read-out device 38 is configured by a flexible disk drive, a CD-ROM drive or a DVD-ROM drive. The read-out device 38 is capable of reading out computer programs or data recorded in a portable recording medium.

For example, the input/output interface 39 is configured by a serial interface such as USB, IEEE 1394, and RS-232C, a parallel interface such as SCSI, IDE, and IEEE 1284, and an analog interface including D/A and ND converters.

The input/output interface 39 is connected to the input device 33 including a keyboard and a mouse. The user can input data to the computer using the input unit 33.

The input/output interface 39 is also connected to the I/O interface 9 of the measurement apparatus 2. Thus, the measurement apparatus 2 can transmit and receive data with the data processing apparatus 4.

The image output interface 40 is connected to the display 32 including a LCD or a CRT. The image output interface 40 allows the display 32 to output an image signal corresponding to the image data from the CPU 34.

[Configuration of the Detection Unit (Flow Cytometer)]

FIG. 5 is a functional block diagram of the flow cytometer 10 which includes the detection unit 6. FIG. 6 is a side view showing an optical system of the flow cytometer 10 which includes the detection unit 6.

As shown in FIG. 5, a lens system 43 of the flow cytometer 10 focuses the laser beam from a semiconductor laser 44 which is a light source on the measurement sample flowing through a flow cell 45. A light collecting lens 46 focuses the forward scattered light of the cells in the measurement sample on a scattered light detector including a photodiode 47.

The lens system 43 is illustrated as a single lens in FIG. 5. Specifically, it has, for example, a configuration shown in FIG. 6.

That is, the lens system 43 of the present embodiment is configured by a collimator lens 43a, a cylindrical lens system (a planoconvex cylindrical lens 43b+a biconcave cylindrical lens 43c), and a condenser lens system (a condenser lens 43d+a condenser lens 43e) in this order from the side of the semiconductor laser 44 (the left-hand side of FIG. 6).

Returning to FIG. 5, a lateral light collecting lens 48 focuses the lateral scattered light and the lateral fluorescence of cells to be measured or nuclei in the cells on a dichroic mirror 49. The dichroic mirror 49 reflects the lateral scattered light on a photomultiplier 50 which is a scattered light detector and transmits the lateral fluorescence to a photomultiplier 51 which is a fluorescence detector. These lights reflect features of the cells and nuclei in the measurement sample.

The photodiode 47 and each of the photomultipliers 50 and 51 convert received light signals into electric signals and output a forward scattered light signal (FSC), a lateral scattered light signal (SSC), and a lateral fluorescence signal (SFL), respectively. These output signals are amplified by a preamplifier (not shown) and sent to the signal processing unit 7 (see FIG. 2) of the measurement apparatus 2.

Each of the signals FSC, SSC, and SFL processed by the signal processing unit 7 of the measurement apparatus 2 is transmitted to the data processing apparatus 4 from the I/O interface 9 by the microprocessor 11.

The CPU 34 of the data processing apparatus 4 (see FIG. 4) creates a scattergram for analyzing the cells and nuclei from each of the signals FSC, SSC, and SFL by executing the operation program 41 and determines whether or not the cells in the measurement sample are abnormal cells, specifically cancerous cells based on the scattergram.

An average size of epithelial cells of the uterine cervix is about 60 μm. The size of nuclei of the epithelial cells of the uterine cervix is from 5 to 7 μm. When the cells become cancerous, the frequency of cell division is abnormally increased and the size of nuclei becomes from 10 to 15 μm. Thus, a N/C ratio (size of nuclei/size of cells) is higher than that of normal cells.

Therefore, there is provided an index for determining whether or not the cells become cancerous by detecting the size of cells and nuclei.

In the present embodiment, the photodiode 47 detects the scattered light from the measurement sample flowing through the flow cell 45 and the photomultiplier 51 detects the fluorescence from the measurement sample flowing through the flow cell 45.

The signal processing unit 7 of the measurement apparatus 2 acquires a pulse width of the scattered light signal which is a value reflecting the size of the cells to be measured from the scattered light signal output from the photodiode 47 and acquires a pulse width of the fluorescence signal which is a value reflecting the size of nuclei of the cells to be measured from the fluorescence signal output the photomultiplier 51.

The CPU 34 of the data processing apparatus 4 which includes an analyzing unit is configured to determine whether or not the cells to be measured are abnormal cells based on the value reflecting the size of the cells to be measured and the value reflecting the size of nuclei of the cells to be measured acquired by the signal processing unit 7.

Specifically, the CPU 34 of the data processing apparatus 4 determines that the cells to be measured are abnormal cells when the peak, nuclear diameter, and area values of the cells to be measured are larger than a predetermined threshold.

[Fluid Circuit of the Preparation Device Unit]

Figure 7:
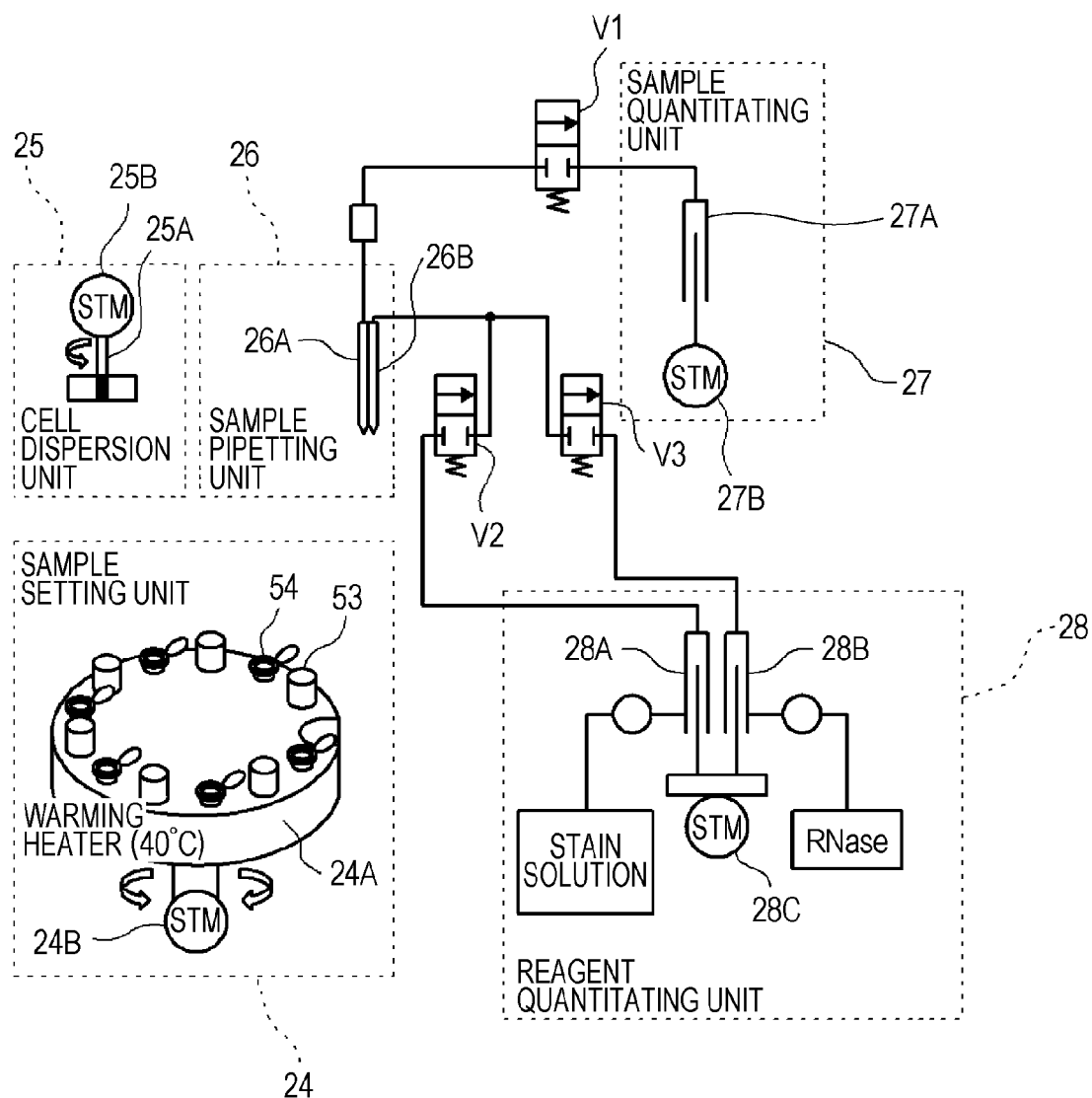
FIG. 7 is a fluid circuit diagram of a preparation device unit.
Figure 8:
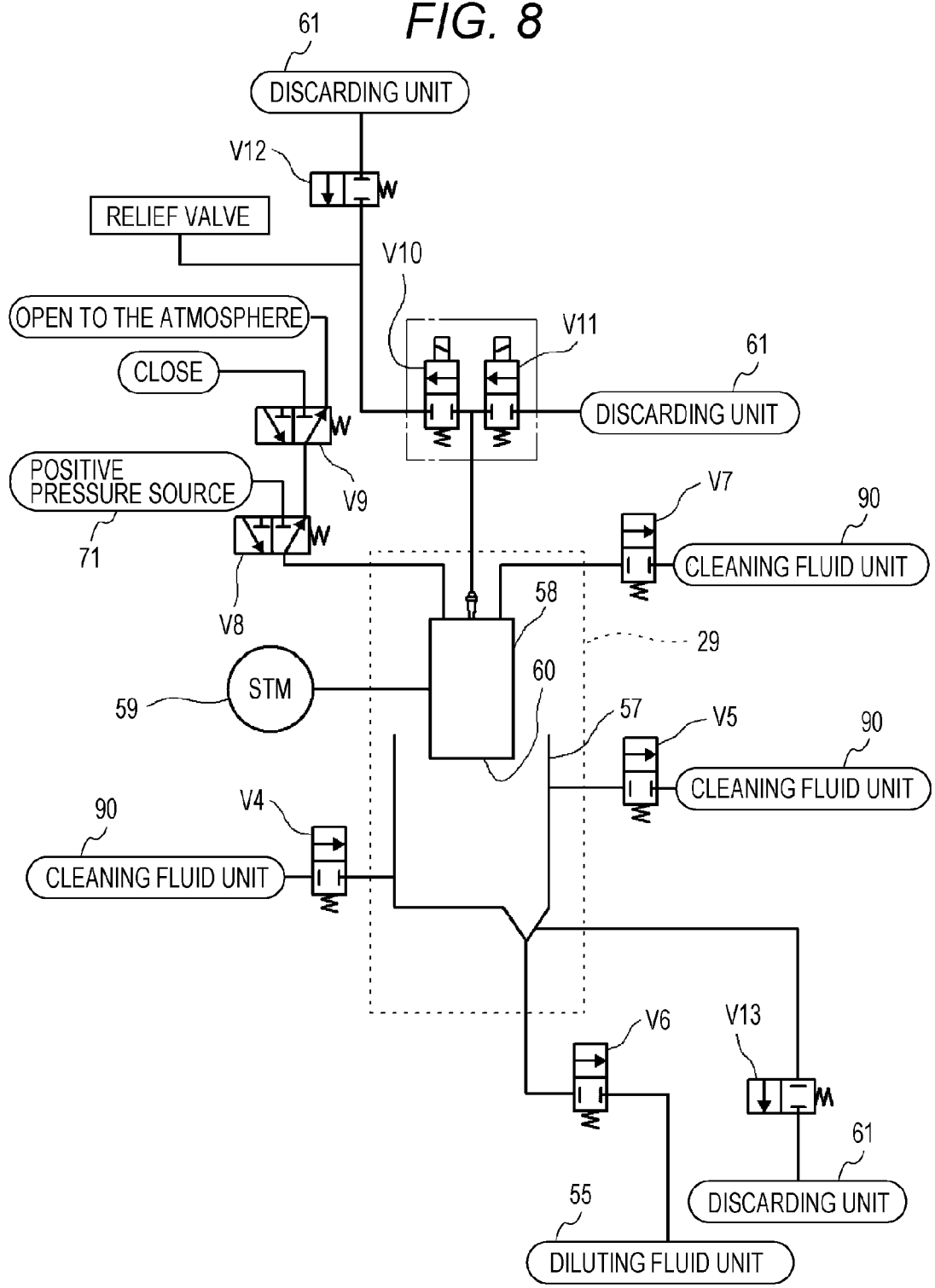
FIG. 8 is a fluid circuit diagram of the preparation device unit.

FIG. 7 is a fluid circuit diagram of the sample setting unit 24 of the preparation device unit 18, the cell dispersion unit 25, the sample pipetting unit 26, the sample quantitating unit 27, and the reagent quantitating unit 28. FIG. 8 is a fluid circuit diagram of the discrimination/substitution unit 29 of the preparation device unit 18.

As shown in FIG. 7, the sample setting unit 24 includes a circular rotatable table 24A and a driving unit 24B which rotates and drives the circular rotatable table 24A. The driving unit 24B includes a stepping motor. A holder capable of setting the biological sample containers 53 which hold the mixed solution of the biological samples and the preservative solution and the measurement sample containers 54 which hold the liquid sample prepared by the discrimination/substitution unit 29 in which the concentration of the cells to be measured is increased is provided in the outer periphery part of the rotating table 24A.

The cell dispersion unit 25 includes a stirring rod 25A which stirs the mixed solution of the biological samples and the preservative solution in the biological sample containers 53 and a driving unit 25B which rotates and drives the stirring rod 25A. The driving unit 25B including a DC motor inserts the stirring rod 25A into the biological sample containers 53 and rotates them. Thus, the mixed solution in the biological sample containers 53 is stirred and thereby the cells contained in the biological samples can be dispersed.

The sample pipetting unit 26 includes a first pipette 26A and a second pipette 26B. The first pipette 26A aspirates the mixed solution of the biological samples and the preservative solution in the biological sample containers 53, moves to a substitution container 57 of the discrimination/substitution unit 29 shown in FIG. 8, and discharges the mixed solution to the substitution container 57. The mixed solution discharged to the substitution container 57 is discriminated and substituted, and a liquid sample in which the concentration of the cells to be measured is increased is prepared from the discriminated and substituted liquid sample containing the cells to be measured. Thereafter, the first pipette 26A aspirates the liquid sample in which the concentration of the cells to be measured is increased from the substitution container 57, moves to the measurement sample container 54 arranged in the sample setting unit 24 of FIG. 7, and discharges the liquid sample to the measurement sample container 54. The second pipette 26B discharges a reagent such as a stain solution which is supplied from the reagent quantitating unit 28 to the measurement sample container 54.

The sample quantitating unit 27 includes a quantitative cylinder 27A and a driving unit 27B including a stepping motor which moves a quantitative piston inserted into the cylinder 27A up and down. The quantitative cylinder 27A is connected to the first pipette 26A through a duct via a direction switching valve V1.

As shown in FIG. 8, the discrimination/substitution unit 29 includes the substitution container 57 having an upwardly opened shape, a piston 58 movable in the substitution container 57 in the up and down direction, and a driving unit 59 including a stepping motor which moves the piston 58 up and down in the substitution container 57.

The substitution container 57 is connected to a cleaning fluid unit 90 through a duct via switching valves V4 and V5. A cleaning fluid is supplied from the cleaning fluid unit 90 to the substitution container 57 via the switching valves V4 and V5. Further, the substitution container 57 is connected to a diluting fluid unit 55 through a duct via a switching valve V6. A diluting fluid is supplied from the diluting fluid unit 55 to the substitution container 57 via the switching valve V6.

The piston 58 includes a hollow cylinder including a filter 60 which does not pass the cells to be measured (epithelial cells) and passes cells having a diameter smaller than that of the cells to be measured (red blood cells, white blood cells, etc.) at the lower part. The piston 58 is connected to a positive pressure source 71 through a duct via a switching valve V8. Thus, a positive pressure can be supplied to the inside of the piston 58 by opening the switching valve V8. The internal space of the piston 58 is connected to the outside via a switching valve V9. The internal space of the piston 58 can be opened to the atmosphere by opening the switching valve V9.

The piston 58 is connected to a discarding unit 61 of filtrate through a duct via switching valves V10 and V12. Thus, a filtrate aspirated from the inside of the piston 58 is discarded to the outside through the switching valves V10 and V12.

The piston 58 is connected to the cleaning fluid unit 90 through a duct via a switching valve V7. The cleaning fluid supplied from the cleaning fluid unit 90 is used for cleaning the piston 58 and the substitution container 57. The cleaning fluid which has cleaned the piston 58 and the inside of the substitution container 57 is discharged to the discarding unit 61 via switching valves V11 and V13.

Returning to FIG. 7, the reagent quantitating unit 28 includes a pair of quantitative cylinders 28A and 28B and a driving unit 28C including a stepping motor which moves quantitative pistons inserted into each of the cylinders 28A and 28B, respectively up and down. Each of the quantitative cylinders 28A and 28B is connected to the second pipette 26B through a duct via supply switching valves V2 and V3, respectively. A reagent quantified by each of the quantitative cylinders 28A and 28B is supplied to the second pipette 26B via the supply switching valves V2 and V3 and discharged to the measurement sample container 54.

Thus, the liquid sample in which the concentration of the cells to be measured is increased, being held in the measurement sample container 54 of the sample setting unit 24, can be mixed with a plurality types of reagents quantified by the quantitating unit 28 in a predetermined amount.

In the present embodiment, there are two types of reagents to be quantified by each of the quantitative cylinders 28A and 28B of the reagent quantitating unit 28. The reagent to be added to the biological samples after weighting it by the quantitative cylinder 28A is a dye solution for performing PI staining. The reagent to be added to the biological samples after weighting it by the other quantitative cylinder 28B is RNase for subjecting cells to an RNA process. The PI staining is performed with propidium iodide (PI) which is a fluorescent staining solution containing a pigment. Since nuclei are selectively stained in the PI staining, the fluorescence from the nuclei can be detected. The RNA process is a process of melting RNA in cells. Since the dye solution stains both RNA and DNA of epithelial cells, RNA is melted by performing the RNA process and is not stained by the dye solution. Therefore, the DNA of a cell nucleus can be accurately measured.

The operation control of the driving units and the switching valves (electromagnetic valves) V1 to V13 in each unit shown in FIGS. 7 and 8 is performed based on a control command from the preparation control unit 16 (microprocessor 19).

[Configuration of the Discrimination/Substitution Unit]

Figure 9:
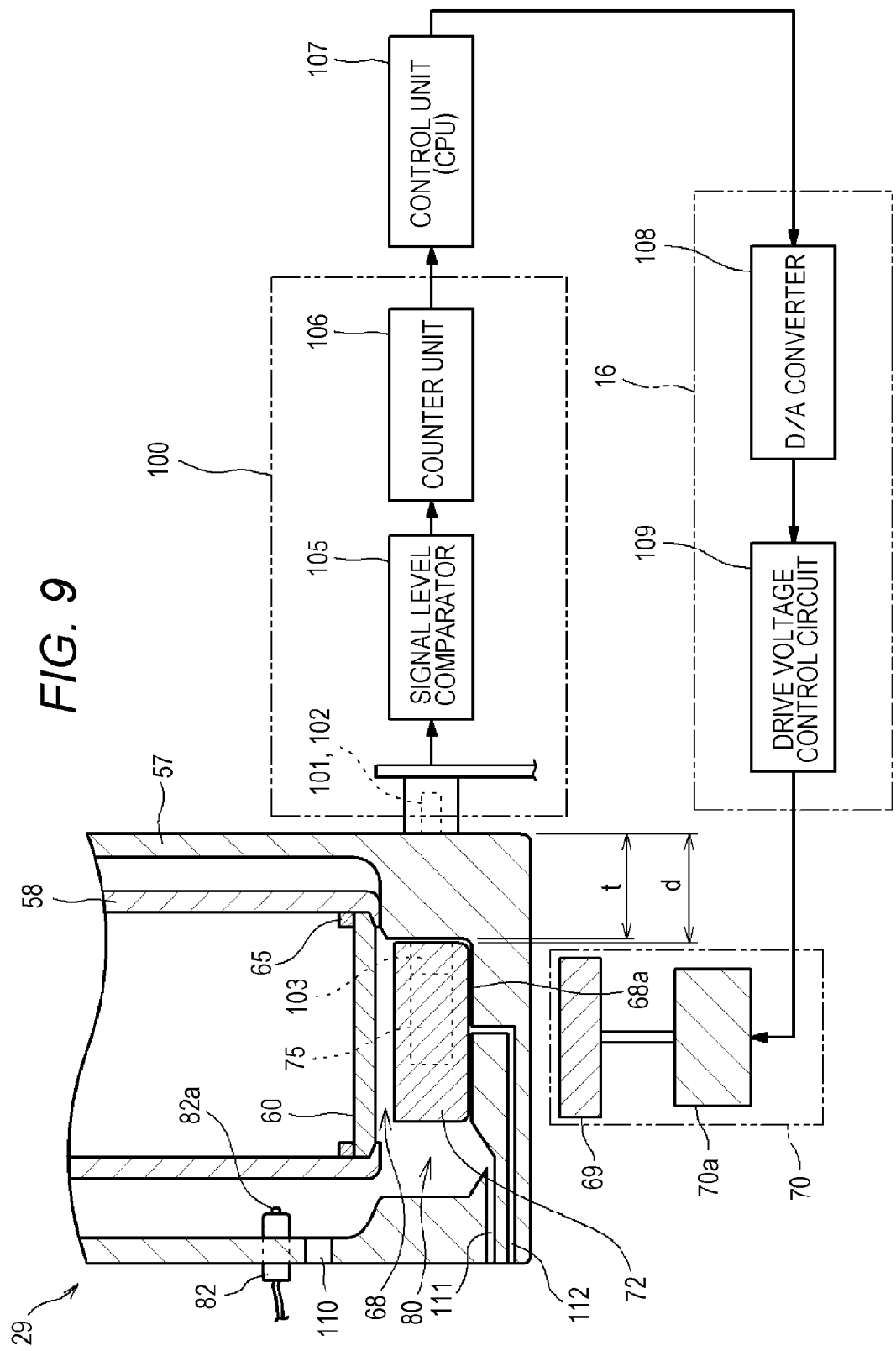
FIG. 9 is a cross sectional explanatory view of a substitution container.

The configuration of the discrimination/substitution unit 29 in the present embodiment will be described with reference to FIG. 9. FIG. 9 is a cross sectional explanatory view of the substitution container 57 in the discrimination/substitution unit 29 of FIG. 8 in the present embodiment.

As shown in FIG. 9, the discrimination/substitution unit 29 of the present embodiment includes the substitution container 57, the piston 58 made of a cylindrical body movable in the substitution container 57 in the up and down direction, a filter 60 for sorting the cells to be measured which is arranged at the lower part of the piston 58 made of a cylindrical body, and a liquid surface detection sensor 82 which detects the surface of the liquid containing the cells to be measured. The discrimination/substitution unit 29 detaches the cells to be measured which has been trapped by the filter 60 from the filter 60 and includes the filter 60, a rotor 72 which is a rotor, a driving unit (magnetic stirrer) 70 which rotates the rotor 72 with a magnetic force, and a rotation information acquiring unit 100 which acquires rotation information of the rotor 72. The driving unit 70 includes a magnet 69 which adsorbs to the rotor 72 with the magnetic force and a driving motor 70a which rotates the magnet 69. The rotation information acquiring unit 100 includes a light emitting unit 101, a light receiving unit 102, a signal level comparator 105, and a counter unit 106. The driving unit (magnetic stirrer) 70 is not particularly limited as long as it rotates the rotor 72 with the magnetic force. For example, known magnetic stirrers can be used.

The substitution container 57 includes a holding chamber 68 which can hold analytes to be analyzed (the cells to be measured) and a condensed sample holding chamber 80 which is communicated with and arranged in the holding chamber. The rotor 72 which moves the cells to be measured contained in the liquid sample from the holding chamber 68 to the condensed sample holding chamber 80 and allows the cells to be measured which has been trapped on the lower surface of the filter 60 to be detached by a shearing force due to rotation is held in the holding chamber 68. The rotor 72 is configured to be rotated by the magnetic force. The magnet 69 for providing the magnetic force to the rotor 72 and the driving motor 70a which is a driving unit for rotating the magnet 69 are provided on the lower side of the bottom of the holding chamber 68.

Figure 10:
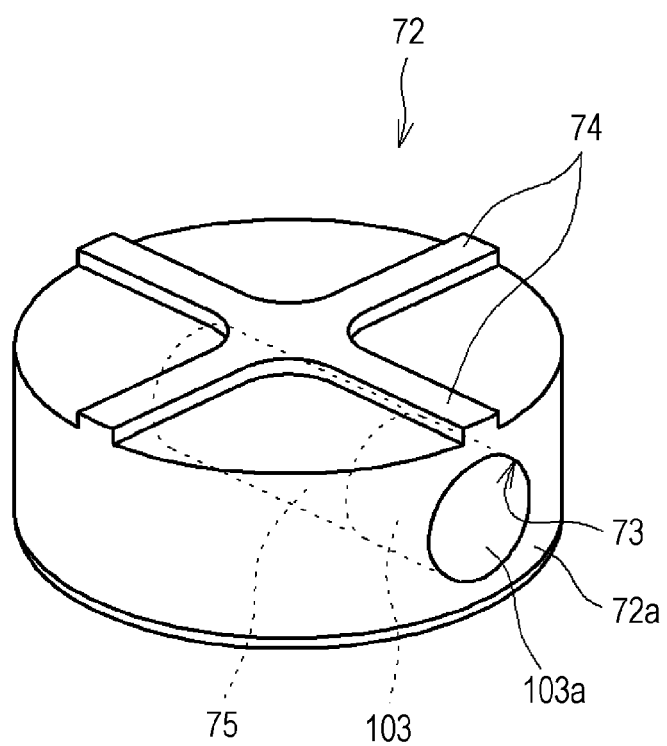
FIG. 10 is a perspective explanatory diagram of a rotor.
Figure 11A:
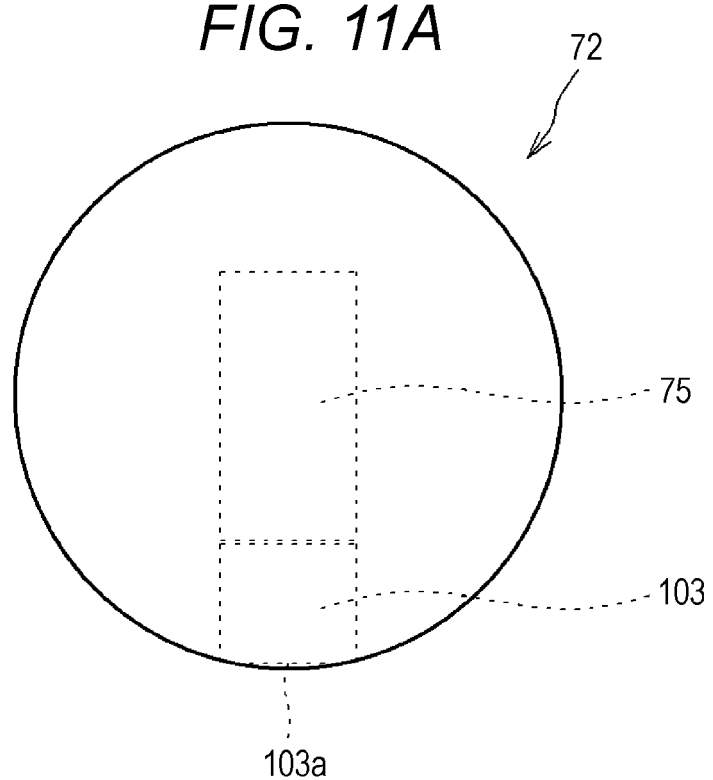
FIG. 11A is a plan view of the rotor shown in FIG. 10
Figure 11B:
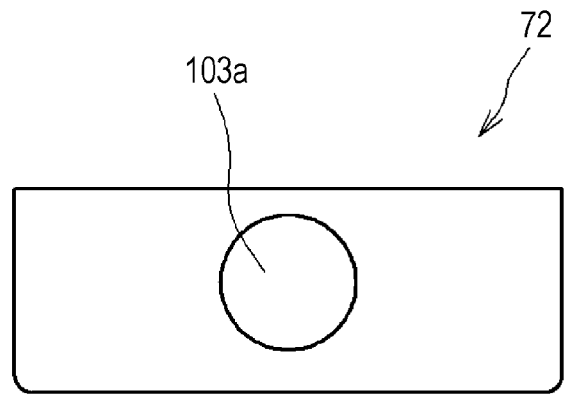
FIG. 11B is a side view of the rotor shown in FIG. 10.

The rotor 72 has a circular cylindrical shape and is made of polychloro-trifluoroethylene (PCTFE), and the like. FIG. 10 is a perspective explanatory diagram showing an example of the rotor 72 in the present embodiment. FIG. 11A is a top view of the rotor 72 in FIG. 10 and FIG. 11B is a side view of the rotor 72 in FIG. 10.

A hole (concave portion) 73 facing the center is formed in the peripheral surface of the rotor 72. A magnet 75 having a round bar shape and a light reflecting unit 103 having a cylindrical shape made of stainless steel are contained in the hole 73. The magnet 69 is rotated by the driving motor 70a, whereby the rotor 72 including the magnet 75 to which the magnetic force is applied from the magnet 69 rotates. An end surface 103a of the light reflecting unit 103 is exposed to the outside and is provided so that the light emitted from the light emitting unit 101 is reflected thereon. The end surface 103a is ground to improve light reflectivity.

In the present embodiment, the magnet 75 has been used to rotate the rotor 72 with the magnetic force generated from the magnetic stirrer 70, however, it is not particularly limited as long as it is a substance having magnetism. Preferably, it is a substance having ferromagnetism (ferromagnetic body). Examples of the ferromagnetic body include a neodymium magnet, a samarium-cobalt magnet, a ferrite magnet, an iron-platinum magnet, an iron-chromium-cobalt magnet, and an alnico magnet.

Two ribs 74 which cross each other are formed on the upper surface of the rotor 72. The ribs 74 are extended to the peripheral edge. The stirring efficiency of the liquid sample present between the lower surface of the filter 60 and the upper surface of the rotor 72 can be improved by forming the ribs 74. As a result, the cells to be measured attached to the lower surface of the filter 60 can be effectively detached from the filter 60. The movement of the cells to be measured to the condensed sample holding chamber to be described later can be performed effectively. The projection height of the ribs 74 is not particularly limited in the present invention, and it is from about 0.3 to 1.0 mm as an indication.

The distance between the lower surface (filtration surface) of the filter 60 and the upper surface of the ribs 74 of the rotor 72 facing the lower surface is not particularly limited and it is preferably 1 mm or less, more preferably 0.6 mm or less. The rotating speed of the magnet 69 which rotates the rotor 72, namely the rotating speed of the driving motor 70a is set preferably to the range of 1000 to 2000 rpm, more preferably to about 1300 rpm.

Returning to FIG. 9, the filter 60 is arranged on the bottom of the piston 58 through a holding fixture 65. The piston 58 serves as a liquid separating unit which separates a liquid into a first liquid which mainly contains the cells to be measured and a second liquid which mainly contains cells having a diameter smaller than that of the cells to be measured by passing the liquid through the filter 60.

In the present embodiment, epithelial cells of the uterine cervix are assumed as the cells to be measured. The size of the epithelial cells is from about 20 to 80 μm (the average size is about 60 μm). The size of red blood cells which are cells smaller than the cells to be measured is from about 7 to 10 μm. Similarly, the size of white blood cells which are cells smaller than the cells to be measured is from about 8 to 15 μm. The size of contaminants such as bacteria is from about 1 to several μm.

Then, the filter 60 in the present embodiment is made of metal having through holes with a diameter smaller than 20 μm (a diameter of 8 to 20 μm) by Chemical Vapor Deposition (CVD) so that epithelial cells do not pass the through holes of the filter 60 even in a state where pressure is applied to the liquid in the substitution container 57 and do not move to the piston 58. The through holes of the CVD filter made of metal have little deformation as compared with other filters made of resin and even a filter made of metal mesh, which is advantageous for improving an aperture ratio.

The pore diameter of the filter 60 has been set to the range of 8 to 20 (m, because many phenomena that the through holes are clogged with the cells and the contaminants at an early stage are observed when the pore diameter is less than 8 (m, and the epithelial cells pass the through holes more often in a state where pressure is applied to the liquid in the substitution container 57 when the pore diameter exceeds 20 (m. The pore diameter of the filter 60 is more preferably around 15 (m.

The liquid surface detection sensor 82 is arranged at the lower part of the substitution container 57 to detect the surface of the first liquid in the substitution container 57. The liquid surface detection sensor 82 is a capacitance type sensor and the distal end of the liquid surface detection sensor 82 is projected from the inner surface of the substitution container 57 to the inner side by about 2 to 3 mm. A sensor unit 82a having a pin shape is provided on the distal end of the projected portion. The liquid surface detection sensor 82 is used to detect that the surface of the first liquid containing the cells to be measured has reached the position, nearly at the bottom of the filter 60.

In the present embodiment, the sensor unit 82a is arranged at the upper side by about 2.0 mm relative to the lower surface of the filter 60 and the aspiration of the second liquid in the piston 58 is stopped after a lapse of predetermined time after the detection signal is received from the sensor unit 82a taking into consideration the influence of the surface tension and the aspiration rate of the second liquid. The sensor unit 82a having a pin shape is arranged at the obliquely upper side, whereby draining of the liquid can be improved and the accuracy of the liquid surface detection can be improved. In this case, an angle to arrange the sensor with respect to a horizontal surface is in the range of about 5 to 90 degrees.

Figure 13:
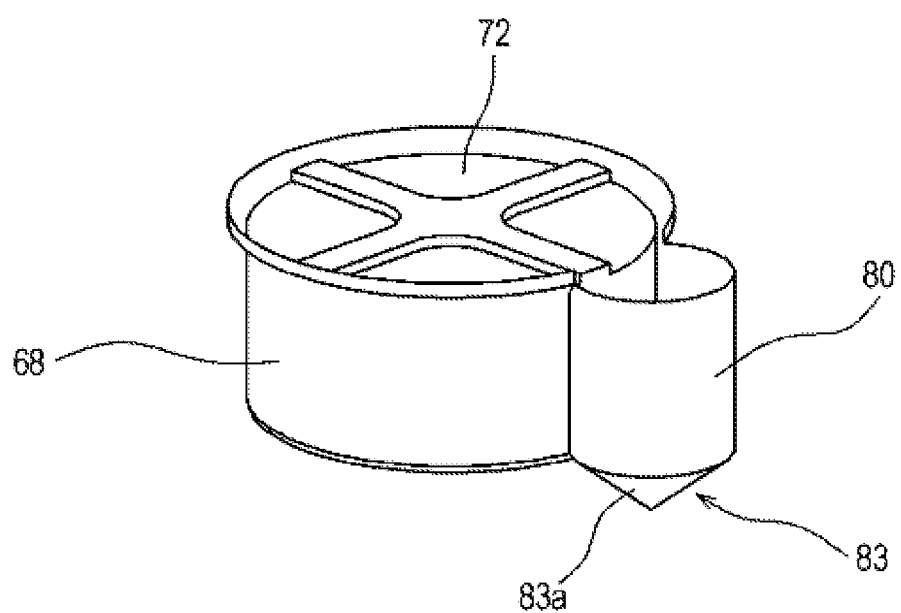
FIG. 13 is an explanatory diagram of an example of a condensed sample holding chamber.

In the present embodiment, the holding chamber 68 and the condensed sample holding chamber 80 communicated with and arranged in the periphery part of the holding chamber 68 are arranged at the bottom of the substitution container 57 (see FIG. 13). The condensed sample holding chamber 80 plays a role in collecting the cells to be measured which have been moved by the rotation of the rotor 72 held in the holding chamber 68. Some of the cells to be measured are trapped and attached to the lower side of the filter 60 by discrimination process to be described later, however, the attached cells to be measured are torn from the lower surface of the filter 60 by the rotation of the rotor 72 and collected into the condensed sample holding chamber 80 communicated with and arranged in the periphery part of the holding chamber 68 by a centrifugal force generated by the rotation of the rotor 72.

Returning to FIG. 9, the rotation information acquiring unit 100 is provided to acquire the rotation information of the rotor 72, specifically, the rotating speed per unit time in order to determine whether or not the rotor 72 is rotating. The rotation information acquiring unit 100 includes the light emitting unit 101 which irradiates the rotor 72 with light, the light receiving unit 102 which detects the light emitted from the light emitting unit 101, the signal level comparator 105 which compares a signal level based on the light detected by the light receiving unit 102 with a reference level, and the counter unit 106 for counting the number of times exceeding the reference level and calculating the rotating speed of the rotor 72 by the signal.

The rotation information of the rotor 72 is acquired based on the number of times that the light receiving unit 102 has detected the light from the light emitting unit 101 reflected by the light reflecting unit 103. Specifically, the light emitted from the light emitting unit 101 toward the rotor 72 rotating is reflected by the light reflecting unit 103 and detected by the light receiving unit 102 only when the light reflecting unit 103 provided in the peripheral surface of the rotor 72 faces the light emitting unit 101. Thus, the rotating speed of the rotor 72 per unit time can be acquired based on the number of times that the light receiving unit 102 has detected the light per unit time.

Figure 12:
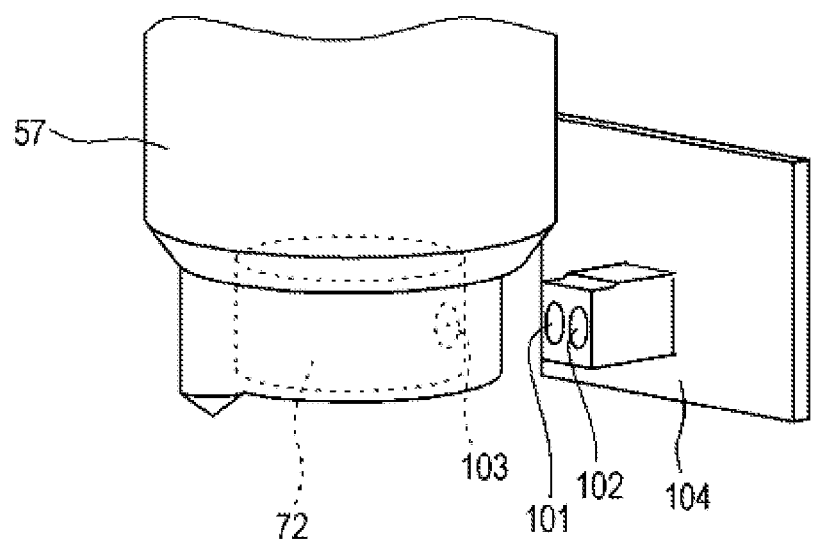
FIG. 12 is a perspective explanatory diagram of a light emitting unit and a light receiving unit.

FIG. 12 is a perspective explanatory diagram showing a configuration of the light emitting unit 101 and the light receiving unit 102. The light emitting unit 101 and the light receiving unit 102 are arranged side by side. The light emitted from the light emitting unit 101 toward the rotor 72 is reflected by the light reflecting unit 103 and detected by the light receiving unit 102 only when the light emitting unit 101 faces the light reflecting unit 103 of the rotor 72. The light emitting unit 101 uses an LED as a light source and is fixed to a supporting unit 104 arranged near the lower part of the substitution container 57 so as to irradiate the outer end surface of the light reflecting unit 103 provided in the peripheral surface of the rotor 72 arranged near the bottom of the substitution container 57 with LED light. The laser can also be used as a light source in place of the LED. Both the LED and the laser have a difference in detection distance. In the case of the laser beam, the detection distance is longer than that of the LED light. Thus, the detection accuracy can be improved and the design flexibility of the substitution container 57 can be improved. When the LED is used, the light emitting unit 101 can be produced in a small size at low cost.

In the present embodiment, the substitution container 57 is made of a vinyl chloride resin which is a light transmittable transparent synthetic resin using the LED as a light source. As shown in FIG. 9, a wall thickness t of a portion to which the light is transmitted is set to, for example, 7.75 mm taking into consideration the detection distance. A distance d from the outer periphery surface of the substitution container 57 (almost the same as the light-irradiated surface of the light emitting unit 101) to the outer end surface of the light reflecting unit 103 (light-reflected surface) is set to, for example, 8.00 mm.

The light reflected by the light reflecting unit 103 is detected by the light receiving unit 102. A signal based on the reflected light from the light reflecting unit 103 which has been detected by the light receiving unit 102 is compared with a reference level by the signal level comparator 105 of the rotation information acquiring unit 100. When the signal level is larger than the reference level, it is counted by the counter unit 106 by PLD, and the like. The rotating speed of the rotor 72 per unit time is calculated based on the resulting value. The rotating speed calculated by the counter unit 106 can be read by a control unit 107 including a CPU. When the rotating speed is lower than a predetermined value, a voltage control signal is supplied to a drive voltage control circuit 109 via a D/A converter 108. A drive voltage of the driving motor 70a is increased so as to increase the rotating speed by the drive voltage control circuit 109 which has received the control signal. When the rotating speed is higher than the predetermined value, the voltage control signal is supplied to the drive voltage control circuit 109 via the D/A converter 108. The drive voltage of the driving motor 70a is reduced so as to decrease the rotating speed by the drive voltage control circuit 109 which has received the control signal. Thus, in the present embodiment, the rotating speed of the rotor 72 can be feedback-controlled. The D/A converter 108 and the drive voltage control circuit 109 are included in the preparation control unit 16 of the sample preparation apparatus 3.

In order to clean the piston 58 and the substitution container 57, a cleaning fluid supplying unit 110 to which the cleaning fluid from the cleaning fluid unit 90 is supplied is provided at the lower side of the liquid surface detection sensor 82. A cleaning fluid discharging unit 111 which leads from the bottommost part of the condensed sample holding chamber 80 to the outside of the substitution container 57 is provided. A cleaning fluid supplying/discharging unit 112 which leads from a bottom surface 68a of the holding chamber 68 to the outside of the substitution container 57 is provided. The cleaning fluid for performing additional cleaning to be described later (cleaning to be performed when the rotation of the rotor 72 is not sufficient) is supplied from the cleaning fluid supplying/discharging unit 112 and discharged. The cleaning fluid when cleaning the piston 58 and the substitution container 57 and the cleaning fluid when performing additional cleaning are discharged from the cleaning fluid discharging unit 111.

Here, a process of the present embodiment in which the mixed solution of the biological samples and the preservative solution is discriminated and the liquid sample in which the concentration of the cells to be measured is increased is prepared from the liquid sample containing the cells to be measured which has been discriminated will be described in detail with reference to the pattern diagram of FIG. 14.

As shown in FIG. 14(a), the piston 58 is lowered so that the filter 60 moves downward from the upper side of the surface of the mixed solution of the biological samples and the preservative solution in the substitution container 57 to the solution.

Then, as shown in FIG. 14(b), the liquid containing the cells to be measured (C1) (the first liquid) remains at the lower side of the filter 60 in the substitution container 57 and the liquid containing cells having a diameter smaller than that of the cells to be measured (C2) (the second liquid) remains at the upper side of the filter 60 (inside of the piston 58).

Thereafter, as shown in FIG. 14(c), the second liquid remaining in the piston 58 is discharged to the outside. In this case, the second liquid is aspirated by applying a negative pressure to the inside of the piston 58, and thus some of the cells to be measured (C1) contained in the first liquid are attached to the lower side of the filter 60.

Figure 14:
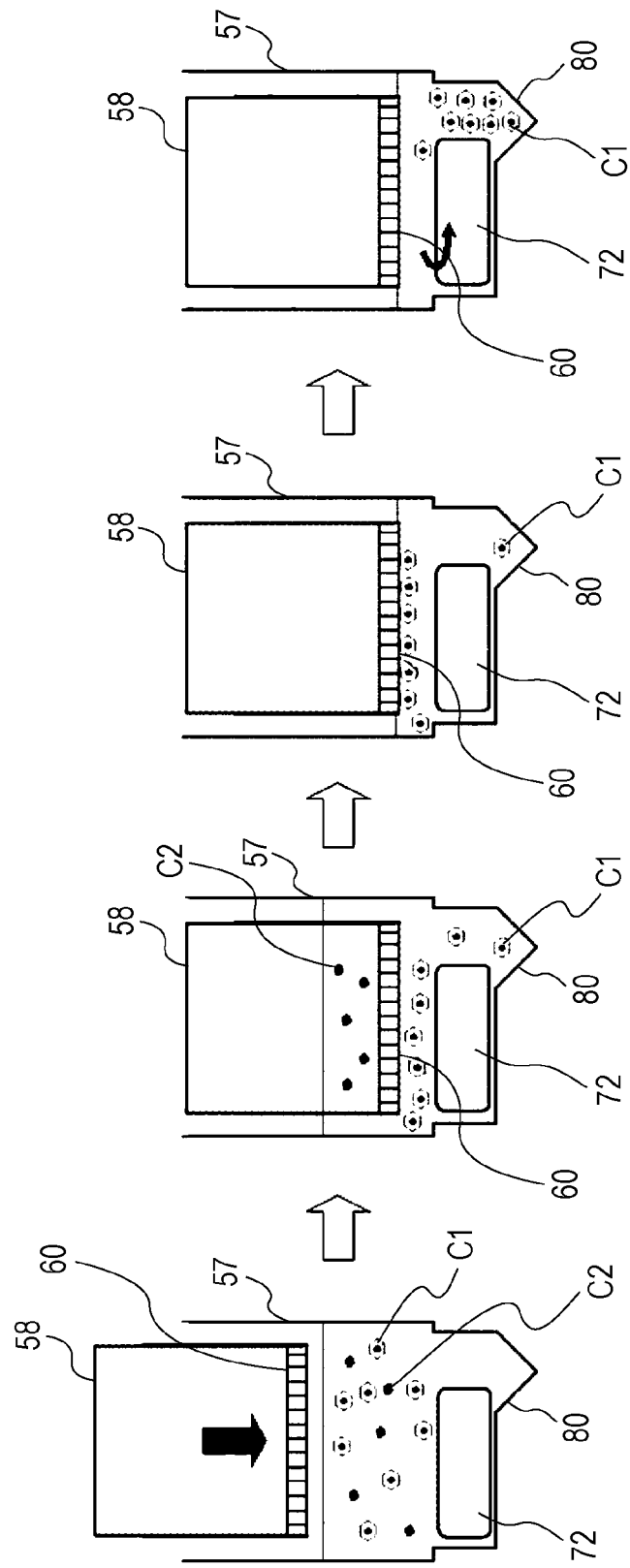
FIG. 14 is a pattern diagram showing a process for concentrating analytes in a discrimination/substitution unit.

As shown in FIG. 14(*d*), the cells to be measured attached to the lower side of the filter 60 are torn by rotating the rotor 72 and the cells to be measured contained in the first liquid are held in the condensed sample holding chamber. The measurement sample with a high concentration of the cells to be measured can be obtained by obtaining the liquid containing the cells to be measured held in the condensed sample holding chamber.

As shown in FIG. 13, a taper 83 whose cross section gradually decreases toward the lower side is formed at the bottom of the condensed sample holding chamber 80. The liquid sample held in the condensed sample holding chamber 80 is aspirated by the first pipette 26A which is a liquid obtaining unit. At that time, the distal end of the first pipette 26A is configured to lower to near the distal end of the taper 83 and to aspirate the liquid sample from near the distal end. Thus, the liquid sample can be used without waste by aspirating the liquid sample in the condensed sample holding chamber 80 as much as possible.

A tilt angle of a tilted surface 83a forming the taper 83 to the horizontal surface is not particularly limited in the present invention, and it is in the range of about 5 to 45 degrees taking into consideration the opening diameter at the distal end of the first pipette 26A. The shape and accumulation of the horizontal section of the condensed sample holding chamber 80 can be determined taking into consideration the amount of the liquid sample required for measurement and a predetermined amount of yield.

[Processing Operation]

Next, the processing operation of the cell analyzer 1 mentioned above will be described.

Figure 15:
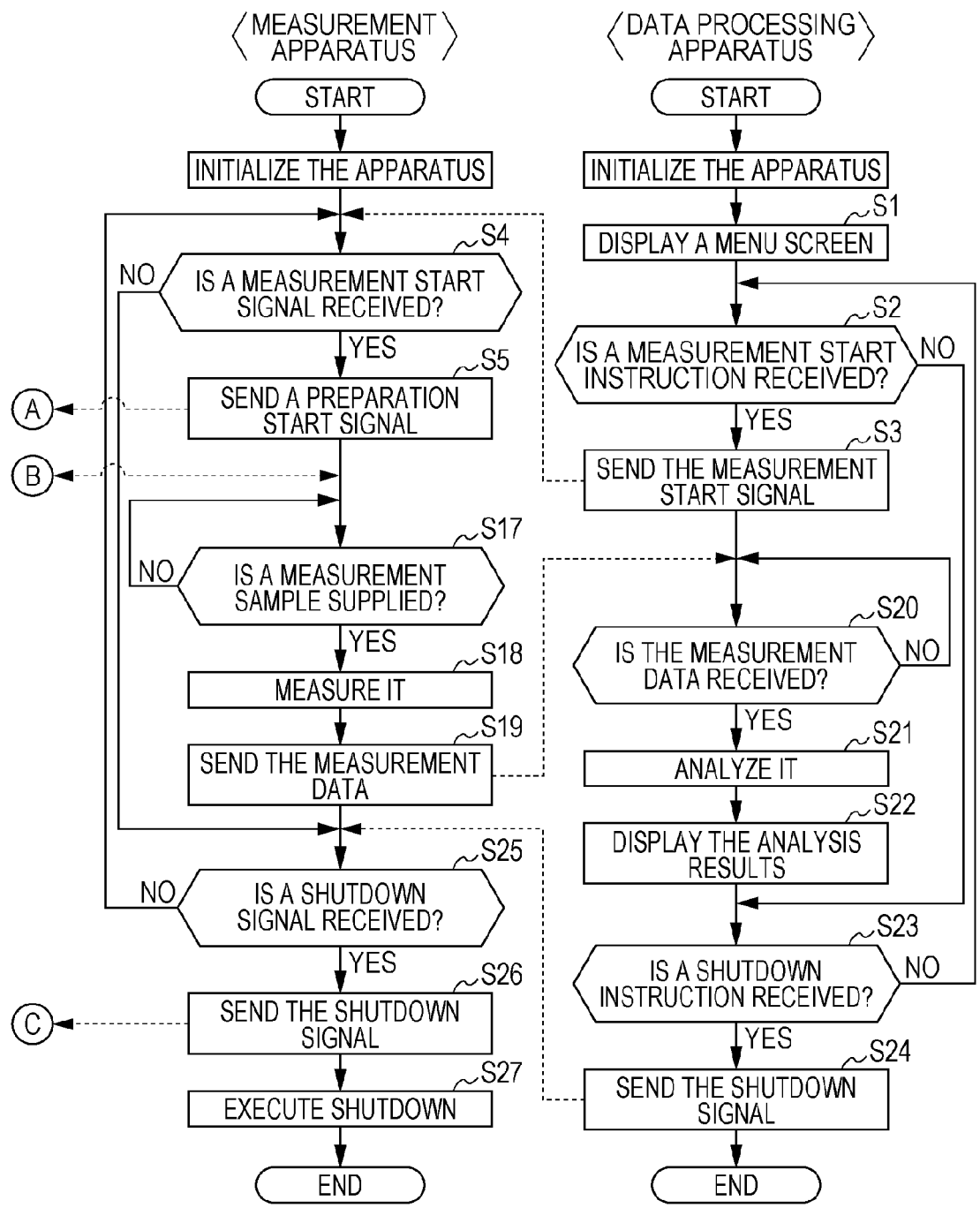
FIG. 15 is a flow chart showing processes which are performed by each control unit of the cell analyzer.
Figure 16:
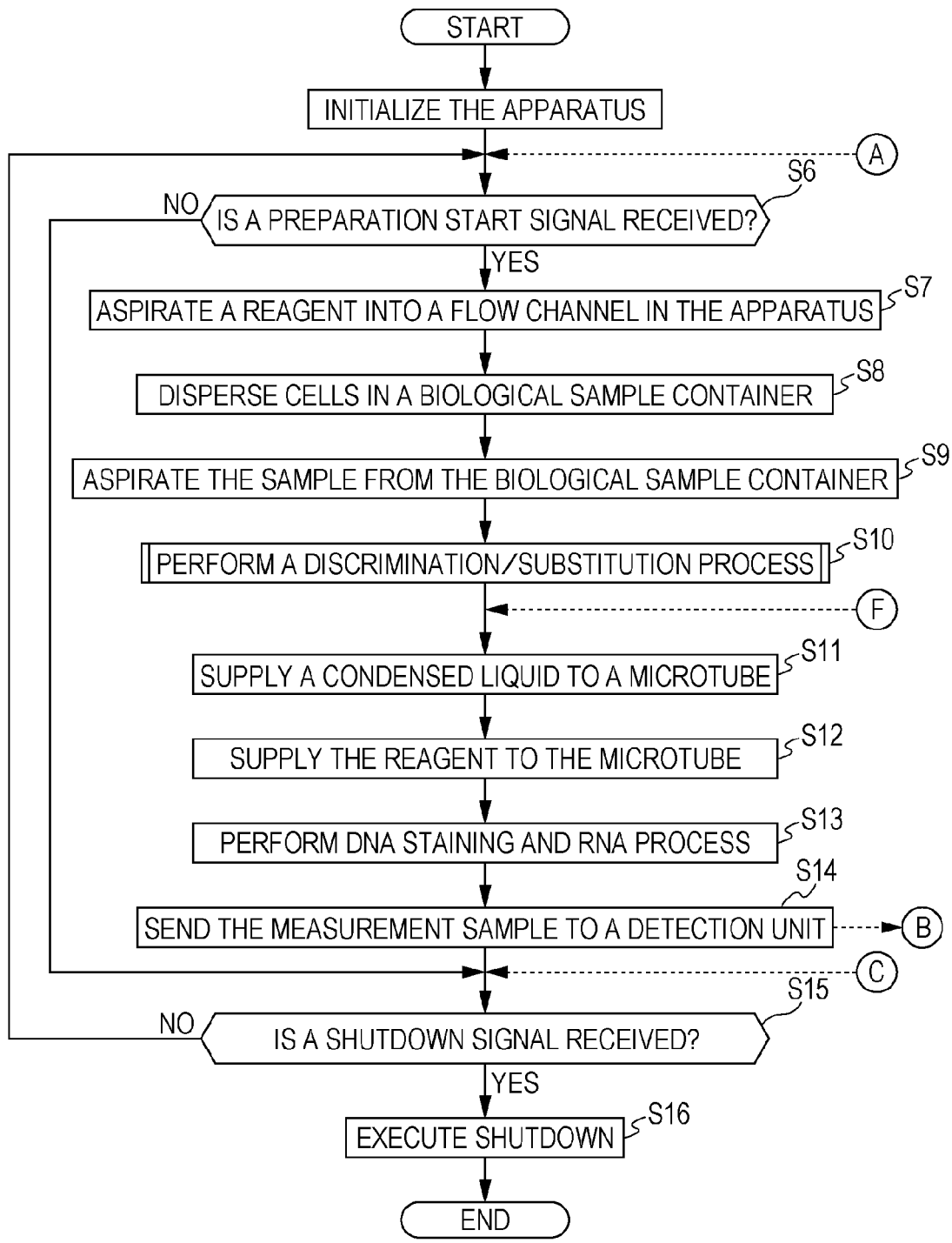
FIG. 16 is a flow chart showing processes which are performed by each control unit of the cell analyzer.

FIGS. 15 and 16 are flow charts showing the process performed by each of the control units 8, 16, and 31 in the cell analyzer 1.

In FIG. 15, a process flow performed by the control unit (processing body) 31 of the data processing apparatus 4 is shown in the right column and a process flow performed by the measurement control unit 8 of the measurement apparatus 2 is shown in the left column. In FIG. 16, a process flow performed by the preparation control unit 16 of the sample preparation apparatus 3 is shown in a line. The process flow is connected to the process flow of FIG. 15 at points A, B, and C. Hereafter, the processing content performed by the cell analyzer 1 will be described with reference to FIGS. 15 and 16.

First, a control unit 31 of the data processing apparatus 4 displays a menu screen on the display 32 (step S1). Thereafter, when a measurement start instruction according to the menu screen is received from the input unit 33 (step S2), the control unit 31 of the data processing apparatus 4 sends a measurement start signal to the measurement apparatus 2 (step S3).

When receiving the measurement start signal (step S4), the measurement control unit 8 of the measurement apparatus 2 sends a preparation start signal to the sample preparation apparatus 3 (step S5 and point A).

When receiving the preparation start signal (step S6), the preparation control unit 16 of the sample preparation apparatus 3 aspirates the reagent to be used for preparation of the measurement sample (stain solution, RNase) into a flow channel in the apparatus and allows the cell dispersion unit 25 to disperse cells in the mixed solution of the biological samples and the preservative solution containing methanol as a main ingredient held in the biological sample container 53 (steps S7 and S8).

Thereafter, the preparation control unit 16 of the sample preparation apparatus 3 allows only a predetermined amount of the mixed solution after dispersion to be aspirated from the biological sample container 53 into the flow channel in the apparatus (step S9), sends the mixed solution to the substitution container 57 of the discrimination/substitution unit 29, and makes the discrimination/substitution unit 29 perform the discrimination/substitution process of the mixed solution (step S10).

[Content of the Discrimination/Substitution Process]

Figure 17:
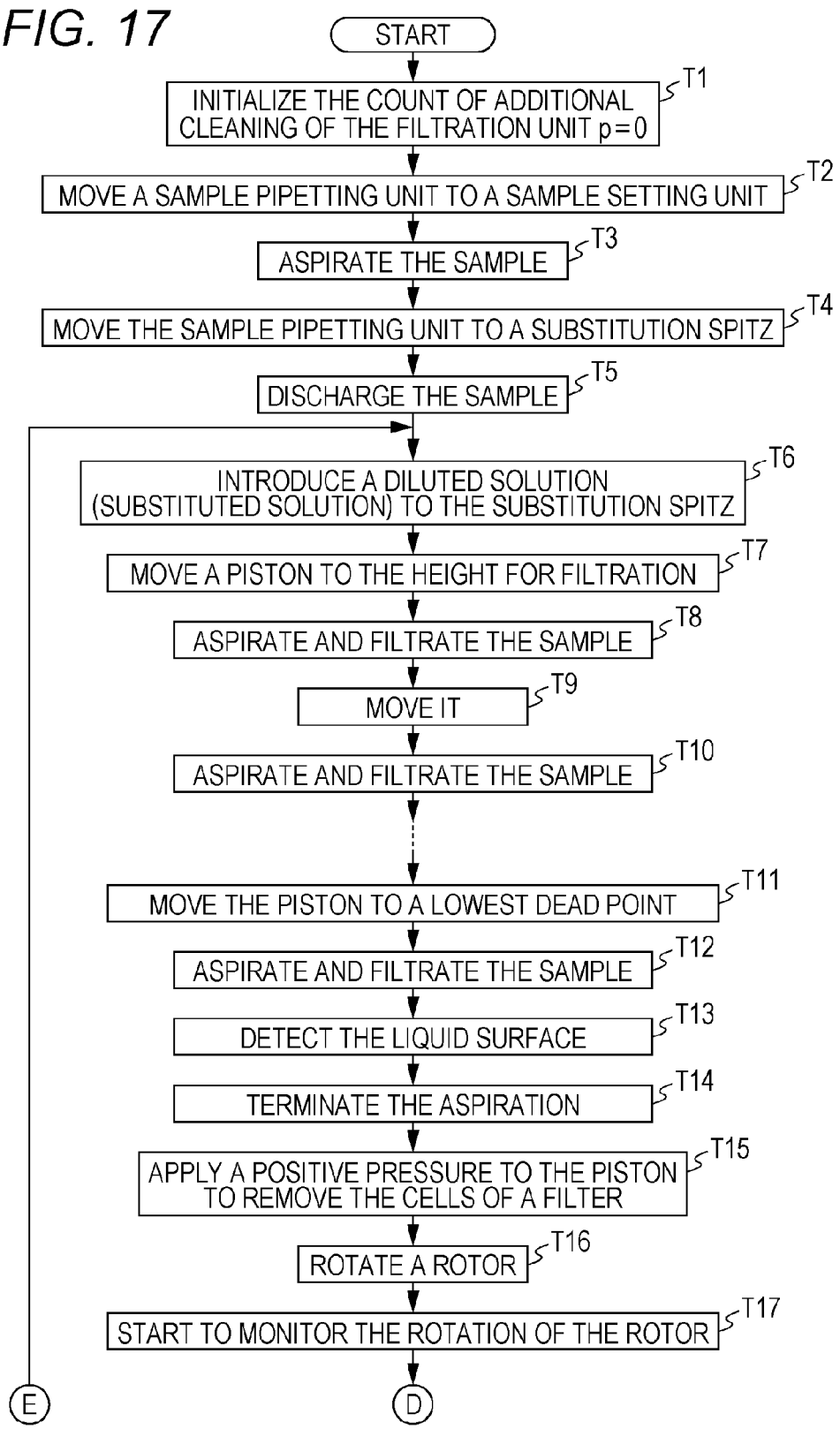
FIG. 17 is a flow chart showing a discrimination/substitution process.
Figure 18:
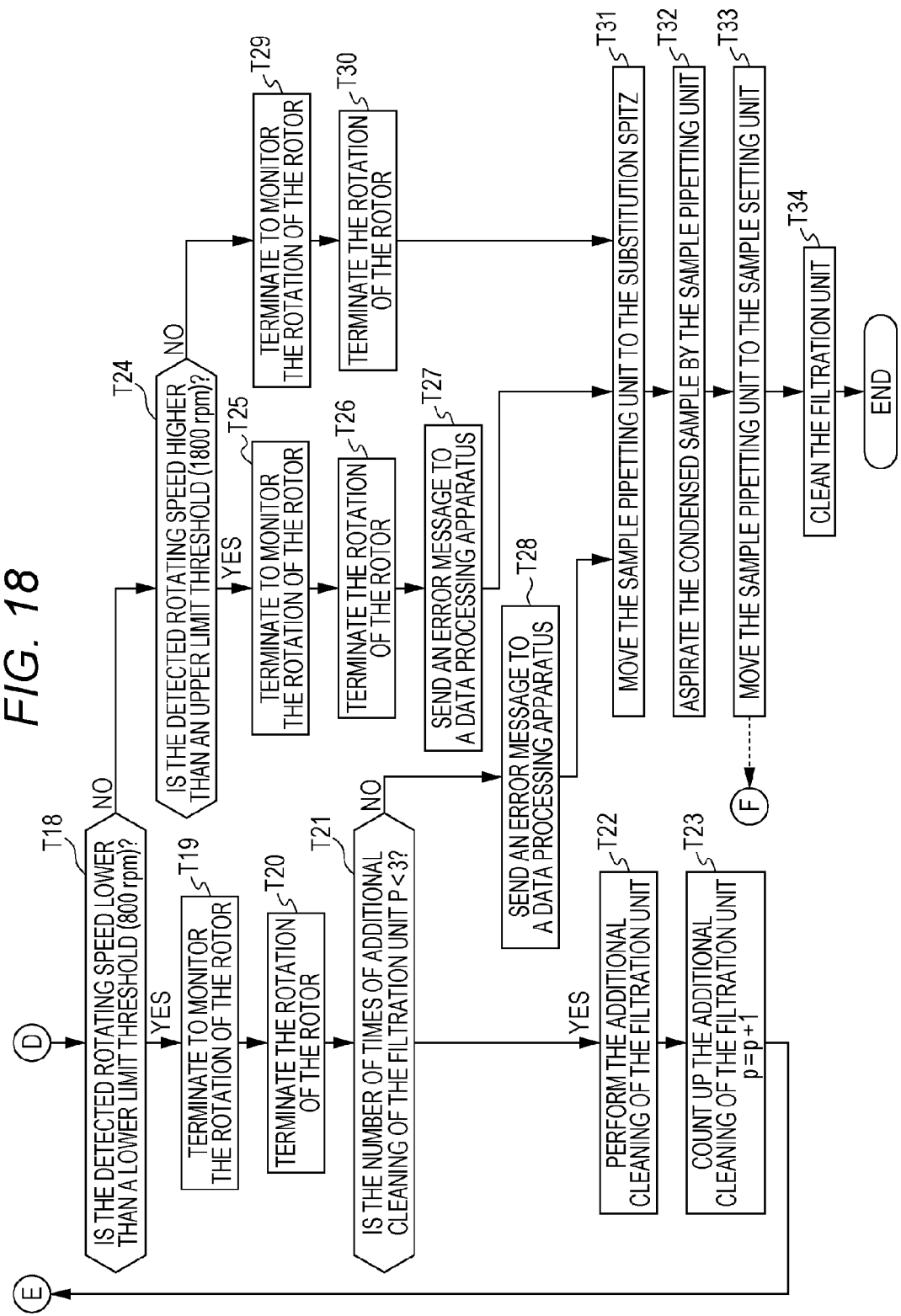
FIG. 18 is a flow chart showing a discrimination/substitution process.

FIGS. 17 and 18 are flow charts showing the discrimination/substitution process (step S10). In the discrimination/substitution process, the cells to be measured are discriminated from the other cells. At that time, the rotation of the rotor 72 which detaches the cells to be measured attached to the filter 60 is monitored, cleaning of a filtration unit (the substitution container 57) is performed when the rotating speed is not sufficient, and rediscrimination (retry) of the cells to be measured is performed.

As shown in FIG. 17, the preparation control unit 16 of the sample preparation apparatus 3 first initializes the count of additional cleaning of the filtration unit (step T1). Then, the preparation control unit 16 of the sample preparation apparatus 3 moves the sample pipetting unit 26 to the sample setting unit 24 (step T2) and makes the first pipette 26A aspirate the mixed solution of the biological samples and the preservative solution in the biological sample container 53 set in the rotating table 24A (step T3).

Then, the preparation control unit 16 moves the sample pipetting unit 26A to the substitution container 57 (step T4) and makes the first pipette 26 discharge the mixed solution aspirated to the substitution container 57 (step T5).

Then, the diluted solution (substituted solution) is introduced from the diluting fluid unit 55 to the substitution container 57 via the valve V6 (step T6).

Then, the piston 58 is moved downward up to a predetermined height for filtration by the driving unit 59 (step T7) and the mixed solution in the substitution container 57 is aspirated into the piston 58 and filtrated (step T8). At the time of aspiration and filtration, the valves V10 and V12 to which a relief valve is connected are used. In this case, the relief valve is set to −5 kpa. Thus, at the time of aspiration and filtration, a pressure of about −3 kpa is applied to the filter 60 arranged at the bottom end of the piston 58. The liquid is aspirated and filtrated with such a weak negative pressure, and thus filtration can be performed without allowing the cells to be measured to pass the filter 60 and to be discharged to the discarding unit 61.

Then, the piston 58 is moved to the lower side by the driving unit 59 (step T9) and the mixed solution in the substitution container 57 is aspirated into the piston 58 and filtrated, similar to step T8 (step T10).

When the movement of the piston 58 and the aspiration and filtration of the sample are repeated at a predetermined number of times and the piston 58 moves to a predetermined lowest dead point (step T11), the mixed solution in the substitution container 57 is aspirated into the piston 58 and filtrated, similar to step T8 (step T12). When the sensor unit 82a of the liquid surface detection sensor 82, which is the capacitance type sensor, arranged in the substitution container 57 detects the liquid surface (step T13), the aspiration is stopped after a lapse of predetermined time (step T14). In this case, the liquid sample containing the cells to be measured is filled in the holding chamber 68 arranged at the bottom of the substitution container 57 and the condensed sample holding chamber 80.

Then, the positive pressure is applied to the piston 58 to remove cells (substances to be analyzed) blocked in the through holes of the filter 60 or attached to the lower surface of the filter 60 and return to the substitution container 57 (the holding chamber 68 and the condensed sample holding chamber 80) (step T15).

Then, in step T16, the rotor 72 is rotated by making the driving motor 70a rotate the magnet 69 to remove the cells to be measured attached to the lower surface of the filter 60, and the cells to be measured contained in the liquid sample in the holding chamber 68 are moved to the direction of the condensed sample holding chamber 80 to allow the cells to be measured to be held in the condensed sample holding chamber 80.

In step T16, after a lapse of predetermined time (e.g. 3 seconds) after the start of rotation of the rotor 72, the monitoring of the rotation of the rotor 72 is started by the rotation information acquiring unit 100 (step T17). As described above, the monitoring of the rotation is performed by detecting the light emitted from the light emitting unit 101 and reflected by the light reflecting unit 103 by the light receiving unit 102.

Then, the preparation control unit 16 determines whether or not the detected rotating speed of the rotor 72 is lower than a predetermined lower limit threshold (step T18). When the set rotating speed is 1300 rpm, the lower limit threshold can be set to, for example, 800 rpm which is lower by 500 rpm than the set rotating speed. On the other hand, an upper limit threshold to be described later can be set to 1800 rpm which is higher by 500 rpm than the set rotating speed.

When determining that the rotating speed of the rotor 72 is lower than 800 rpm which is the predetermined lower limit threshold, the preparation control unit 16 advances the process to step T19 and terminates the monitoring of the rotation of the rotor 72.

Then, the preparation control unit 16 terminates the rotation of the rotor 72 in step T20.

Then, the preparation control unit 16 determines whether or not the number of times of additional cleaning of the filtration unit is less than three times in step T21. When determining that the number of times of additional cleaning of the filtration unit is less than three times, the preparation control unit 16 performs the additional cleaning of the filtration unit (step T22). On the other hand, when determining that the number of times of additional cleaning of the filtration unit is three times or more, the preparation control unit 16 advances the process to step T28 and sends an error message to the data processing apparatus 4 in step T28.

After completion of the additional cleaning of the filtration unit, the preparation control unit 16 counts up the additional cleaning of the filtration unit in step T23, returns to step T6, and allows the diluted solution (substituted solution) to be reintroduced from the diluting fluid unit 55 in the substitution container 57 via the valve V6. The processes after step T7 as described above are repeated.

In step T18, when the preparation control unit 16 determines that the rotating speed of the rotor 72 is higher than the predetermined lower limit threshold ("NO" in step T18), the preparation control unit 16 determines whether or not the detected rotating speed of the rotor 72 is higher than a predetermined upper limit threshold in step T24.

When determining that the rotating speed of the rotor 72 is higher than 1800 rpm which is the predetermined upper limit threshold, the preparation control unit 16 advances the process to step T25 and terminates the monitoring of the rotation of the rotor 72. Then, the preparation control unit 16 terminates the rotation of the rotor 72 in step T26, advances the process to step T27, and sends the error message to the data processing apparatus 4 in step T27. On the other hand, when determining that the rotating speed of the rotor 72 is lower than 1800 rpm which is the predetermined upper limit threshold, the preparation control unit 16 advances the process to step T29 and terminates the monitoring of the rotation of the rotor 72. Then, the preparation control unit 16 terminates the rotation of the rotor 72 in step T30 and advances the process to step T31.

The preparation control unit 16 moves the sample pipetting unit 26 to the substitution container 57 (step T31), makes the first pipette 26A aspirate the condensed sample from the condensed sample holding chamber 80 (step T32), and moves the sample pipetting unit 26 to the sample setting unit (step T33).

Then, the preparation control unit 16 cleans the filtration unit (step T34). In this case, the cleaning fluid is supplied from the cleaning fluid supplying unit 110 for filters to the substitution container 57.

The liquid sample mainly containing the cells to be measured (epithelial cells) in which the number of cells other than the cells to be measured is reduced can be obtained by the discrimination/substitution process. In the discrimination/substitution process, the concentration of methanol contained in the preservative solution in the liquid supplied from the biological sample container 53 to the substitution container 57 (the mixed solution of the biological samples and the preservative solution) can be diluted by substituting most of the preservative solution with the diluted solution. Thus, in a DNA staining process to be described later, the influence of the preservative solution can be reduced and DNA of the cells to be measured can be well stained.

In the discrimination/substitution process, since the substitution process of the preservative solution and the diluted solution can be performed while performing the discrimination process of cells, the discrimination process and the substitution process can be performed in a shorter time than when these two processes are performed separately.

In the discrimination/substitution process, the cells to be measured (epithelial cells) attached to the lower surface of the filter 60 are detached by the shearing force by rotating the rotor 72 to allow the detached cells to be suspended in the first liquid of the lower side of the filter 60, and the cells to be measured (epithelial cells) blocked in the through holes of the filter 60 are removed by applying pressure from the upper side of the filter 60 to the through holes of the filter 60 to allow the cells to be suspended in the first liquid of the lower part of the filter 60. Thus, the cells to be measured (epithelial cells) attached to the filter can be efficiently recovered without loss of them.

[Preparation of the Measurement Sample]

Returning to FIG. 16, the preparation control unit 16 of the sample preparation apparatus 3 supplies the condensed sample from the sample pipetting unit 26 moved to the sample setting unit to the measurement sample container 54 (step S11).

Then, the preparation control unit 16 of the sample preparation apparatus 3 sends the stain solution and RNase stored in the apparatus from the reagent quantitating unit 28 to the second pipette 26B, the second pipette 26B supplies the stain solution and RNase which have been sent to the measurement sample container 54 (step S12) and produces the measurement sample by performing DNA staining and RNA process in the measurement sample container 54 (step S13).

After the completion of the process, the obtained measurement sample is quantified by the sample quantitating unit 27 through the first pipette 26A and supplied to the detection unit 6 of the measurement apparatus 2 after quantification (step S14 and point B).

The preparation control unit 16 of the sample preparation apparatus 3 always determines whether or not the shutdown signal from the measurement apparatus 2 is received (step S15 and point C), returns to step S6 for determining whether or not the preparation start signal is received when the signal is not received, and executes the shutdown to terminate the sample preparation process when the signal is received (step S16).

[Measurement by the Measurement Apparatus and its Data Analysis]

Returning to FIG. 15, after sending the preparation start signal, the measurement control unit 8 of the measurement apparatus 2 always determines whether or not the measurement sample is supplied from the sample preparation apparatus 3 (step S17).

When the measurement sample is sent from the sample preparation apparatus 3 (point B), the control unit 8 of the measurement apparatus 2 sends the measurement sample to the flow cell 45 of a measurement unit 14, performs the measurement of cells of the measurement sample (step S18), and sends the measurement data to the data processing apparatus 4 (step S19).

On the other hand, after sending the measurement start signal, the control unit 31 of the data processing apparatus 4 always determines whether or not the measurement data is received from the measurement apparatus 2 (step S20).

When receiving the measurement data from the measurement apparatus 2, the control unit 31 of the data processing apparatus 4 analyzes the cells and nuclei using the measurement data and determines whether or not the cells in the measurement sample become cancerous (step S21).

The control unit 31 of the data processing apparatus 4 displays the analysis results on the display 32 (step S22) and determines whether or not a shutdown instruction is input by the user (step S23).

When the shutdown instruction is input, the control unit 31 of the data processing apparatus 4 sends a shutdown signal to the measurement apparatus 2 (step S24).

The control unit 8 of the measurement apparatus 2 always determines whether or not the shutdown signal from the data processing apparatus 4 is received (step S25), returns to step S4 for determining whether or not the measurement start signal is received when the signal is not received, transfers the shutdown signal to the sample preparation apparatus 3 when the signal is received (step S26), and executes the shutdown to terminate the measurement process (step S27).

In the embodiments, the rotation of the rotor 72 is monitored, when performing the discrimination/substitution process, however, the present invention is not limited thereto. For example, when activating the apparatus or when terminating the measurement, the monitoring of the rotation of the rotor 72 can also be performed. When terminating the measurement, the time when the waiting time to the next measurement is long is included (for example, when there is a waiting time of 1 hour or more) except when terminating a daily measurement. Hereinafter, procedures for monitoring the rotation of the rotor 72 after the measurement (FIG. 19) and at the time of activating the apparatus (FIG. 20) will be described based on the flow charts.

After the Measurement (Adhesion-preventive Process)

Figure 19:
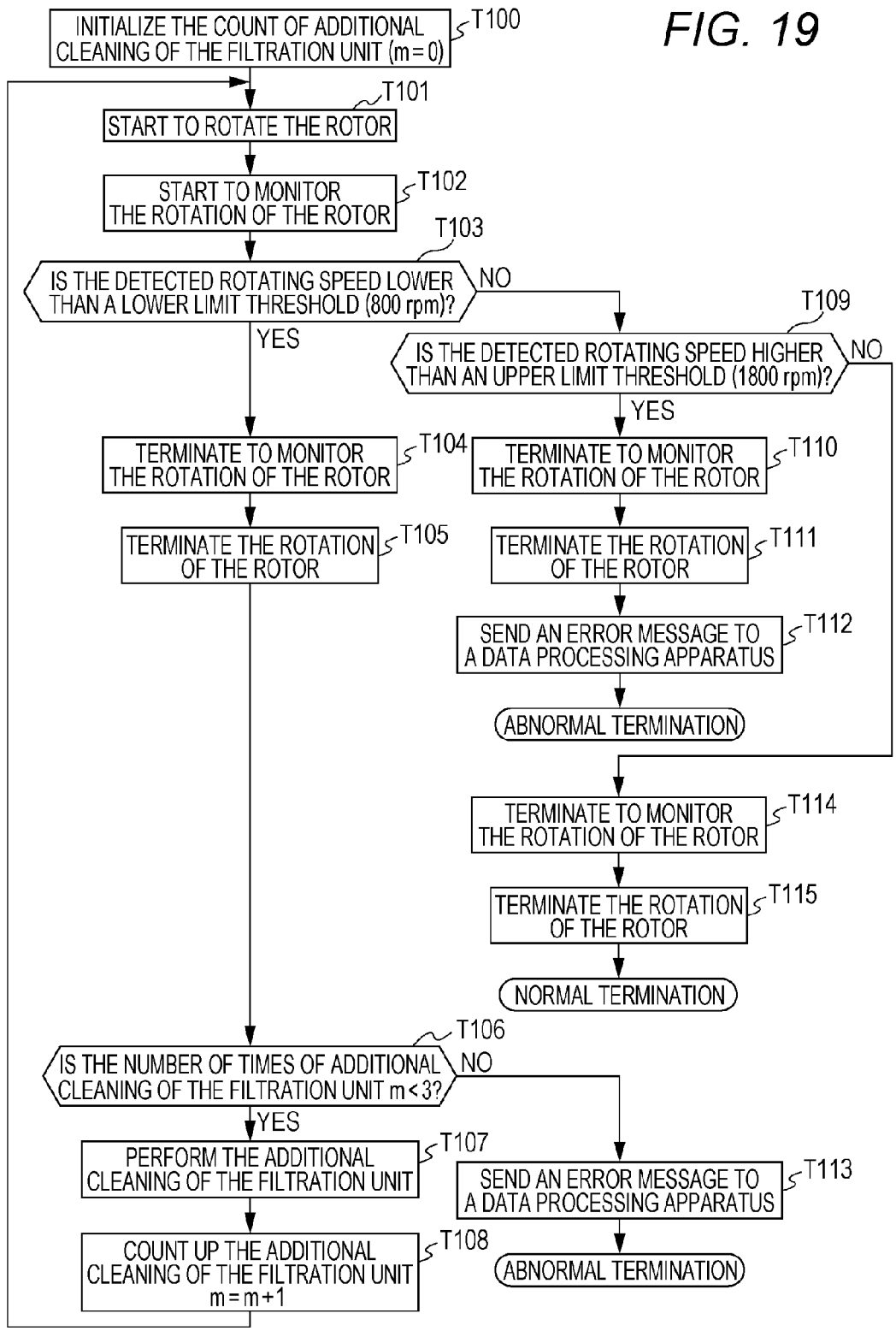
FIG. 19 is a flow chart for checking the rotation after the measurement.

FIG. 19 is a flow chart showing the procedure for monitoring the rotation of the rotor 72 after the measurement. When an interval until the next measurement is performed is long, for example, when terminating the daily measurement, an insufficient cleaning may cause the rotor 72 to adhere to the wall surface of the substitution container 57. A normal operation of the rotor 72 at the next measurement can be ensured by checking the rotation of the rotor 72 after the measurement and performing the additional cleaning of the filtration unit, if necessary.

The process until the filtration unit is cleaned is the same as the process in the discrimination/substitution process described in FIGS. 17 and 18. The preparation control unit 16 of the sample preparation apparatus 3 initializes the count (m=0) of additional cleaning of the filtration unit in step T100 when cleaning the filtration unit.

When terminating the cleaning of the filtration unit, the preparation control unit 16 rotates the rotor 72 by making the driving motor 70a rotate the magnet 69 in step T101.

In step T101, after a lapse of predetermined time (e.g. 3 seconds) after the start of rotation of the rotor 72, the monitoring of the rotation of the rotor 72 is started by the rotation information acquiring unit 100 (step T102). As described above, the monitoring of the rotation is performed by detecting the light emitted from the light emitting unit 101 and reflected by the light reflecting unit 103 by the light receiving unit 102.

Then, the preparation control unit 16 determines whether or not the detected rotating speed of the rotor 72 is lower than a predetermined lower limit threshold (step T103). When the set rotating speed is 1300 rpm, the lower limit threshold can be set to, for example, 800 rpm which is lower by 500 rpm than the set rotating speed. On the other hand, an upper limit threshold to be described later can be set to 1800 rpm which is higher by 500 rpm than the set rotating speed.

When determining that the rotating speed of the rotor 72 is lower than 800 rpm which is the predetermined lower limit threshold, the preparation control unit 16 advances the process to step T104 and terminates the monitoring of the rotation of the rotor 72.

Then, the preparation control unit 16 terminates the rotation of the rotor 72 in step T105.

Then, the preparation control unit 16 determines whether or not the number of times of additional cleaning of the filtration unit is less than three times in step T106. When determining that the number of times of additional cleaning of the filtration unit is less than three times, the preparation control unit 16 performs the additional cleaning of the filtration unit (step T107). On the other hand, when determining that the number of times of additional cleaning of the filtration unit is three times or more, the preparation control unit 16 advances the process to step T113 and sends an error message to the data processing apparatus 4 in step T113 (abnormal termination).

After completion of the additional cleaning of the filtration unit, the preparation control unit 16 counts up (m=m+1) the additional cleaning of the filtration unit in step T108, returns to step T101, and starts the rotation of the rotor 72 again. The processes after step T102 as described above are repeated.

In step T103, when the preparation control unit 16 determines that the rotating speed of the rotor 72 is higher than the predetermined lower limit threshold ("NO" in step T103), the preparation control unit 16 determines whether or not the detected rotating speed of the rotor 72 is higher than a predetermined upper limit threshold in step T109.

When determining that the rotating speed of the rotor 72 is higher than 1800 rpm which is the predetermined upper limit threshold, the preparation control unit 16 advances the process to step T110 and terminates the monitoring of the rotation of the rotor 72. Then, the preparation control unit 16 terminates the rotation of the rotor 72 in step T111, advances the process to step T112, and sends the error message to the data processing apparatus 4 in step T112 (abnormal termination). On the other hand, when determining that the rotating speed of the rotor 72 is lower than 1800 rpm which is the predetermined upper limit threshold in step T109, the preparation control unit 16 advances the process to step T114 and terminates the monitoring of the rotation of the rotor 72. Then, the preparation control unit 16 terminates the rotation of the rotor 72 in step T115. Then, it is normally terminated.

At the Time of Activating the Apparatus

Figure 20:
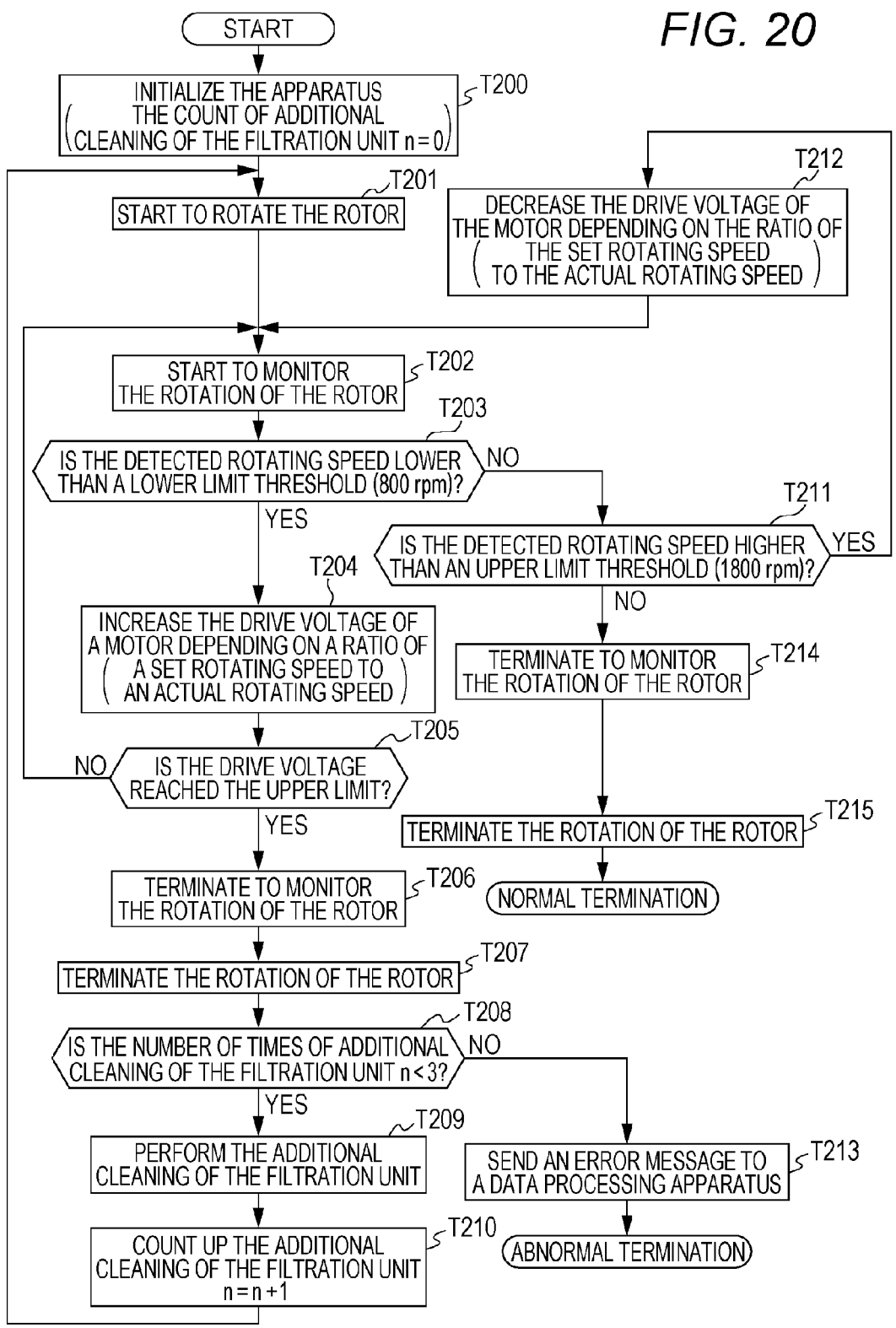
FIG. 20 is a flow chart for checking the rotation at the time of activating the apparatus.

FIG. 20 is a flow chart showing the procedure for monitoring the rotation of the rotor 72 at the time of activating the apparatus. The measurement can be performed smoothly by checking the rotation state of the rotor 72 before activating the apparatus.

When a start switch is pushed by the user, initialization of the apparatus is performed in step T200 and the count of additional cleaning of the filtration unit is also initialized (n=0).

When the initialization is terminated, the preparation control unit 16 rotates the rotor 72 by applying a predetermined voltage to the driving motor 70a to rotate the magnet 69 in step T201.

In step T201, after a lapse of predetermined time (e.g. 3 seconds) after the start of rotation of the rotor 72, the monitoring of the rotation of the rotor 72 is started by the rotation information acquiring unit 100 (step T202). As described above, the monitoring of the rotation is performed by detecting the light emitted from the light emitting unit 101 and reflected by the light reflecting unit 103 by the light receiving unit 102.

Then, the preparation control unit 16 determines whether or not the detected rotating speed of the rotor 72 is lower than a predetermined lower limit threshold (step T203). When the set rotating speed is 1300 rpm, the lower limit threshold can be set to, for example, 800 rpm which is lower by 500 rpm than the set rotating speed. On the other hand, an upper limit threshold to be described later can be set to 1800 rpm which is higher by 500 rpm than the set rotating speed. As for the lower limit threshold, the rotating speed for indexing whether or not the rotor is adhering may be set as a threshold. In the present embodiment, when the rotating speed of the rotor is 800 rpm or less, there is a possibility that the rotor is adhering. Thus, the lower limit threshold is set to 800 rpm.

When determining that the rotating speed of the rotor 72 is lower than 800 rpm which is the predetermined lower limit threshold, the preparation control unit 16 advances the process to step T204 and increases the drive voltage of the driving motor 70a depending on a predetermined determination value, for example, a ratio obtained by dividing the set rotating speed of the rotor 72 by an actual rotating speed of the rotor 72 (the actual number of rotation) in step T204. In this case, since the ratio becomes higher with a lower actual rotating speed than the set rotating speed, the control to increase an amount of increase of the drive voltage of the driving motor 70a is performed with a higher level of the ratio.

Then, the preparation control unit 16 determines whether or not the drive voltage of the driving motor 70a increased in step T204 reaches the upper limit in step T205. When determining that the drive voltage of the driving motor 70a increased in step T204 reaches the upper limit, the preparation control unit 16 advances the process to step T206 and terminates the monitoring of the rotation of the rotor 72. Then, the preparation control unit 16 terminates the rotation of the rotor 72 in step T207 and advances the process to step T208. On the other hand, when determining that the drive voltage of the driving motor 70a does not reach the upper limit, the preparation control unit 16 returns to step T202. The rotation of the rotor 72 is continuously monitored, and the processes after step T203 as described above are repeated.

Then, the preparation control unit 16 determines whether or not the number of times of additional cleaning of the filtration unit is less than three times in step T208. When determining that the number of times of additional cleaning of the filtration unit is less than three times, the preparation control unit 16 performs the additional cleaning of the filtration unit (step T209). On the other hand, when determining that the number of times of additional cleaning of the filtration unit is three times or more, the preparation control unit 16 advances the process to step T213 and sends an error message to the data processing apparatus 4 in step T213 (abnormal termination).

After completion of the additional cleaning of the filtration unit, the preparation control unit 16 counts up (n=n+1) the additional cleaning of the filtration unit in step T210, returns to step T201, and starts the rotation of the rotor 72 again. The processes after step T202 as described above are repeated.

In step T203, when the preparation control unit 16 determines that the rotating speed of the rotor 72 is higher than the predetermined lower limit threshold ("NO" in step T203), the preparation control unit 16 determines whether or not the detected rotating speed of the rotor 72 is higher than a predetermined upper limit threshold in step T211.

When determining that the rotating speed of the rotor 72 is higher than 1800 rpm which is the predetermined upper limit threshold, the preparation control unit 16 advances the process to step T212 and decreases the drive voltage of the driving motor 70a depending on a predetermined determination value, for example, a ratio obtained by dividing the set rotating speed by an actual rotating speed of the rotor 72 (the actual number of rotation) in step T212. In this case, the ratio becomes lower with a higher actual rotating speed than the set rotating speed. However, contrary to step T204, the control to increase an amount of decrease of the drive voltage of the driving motor 70a is performed with a lower level of the ratio. Then, the process is returned to step T202, the rotation of the rotor 72 is continuously monitored, and the processes after step T203 as described above are repeated.

On the other hand, when determining that the rotating speed of the rotor 72 is lower than 1800 rpm which is the predetermined upper limit threshold in step T211, the preparation control unit 16 advances the process to step T214 and terminates the monitoring of the rotation of the rotor 72. Then, the preparation control unit 16 terminates the rotation of the rotor 72 in step T215. Then, it is normally terminated.

In the example shown in FIG. 20, the rotation of the rotor 72 can be normally maintained by controlling the drive voltage to the driving motor 70a based on the rotating speed which is the rotation information of the rotor 72 and performing the additional cleaning of the filtration unit.

[Other Variants]

The disclosed embodiments are illustrative and not restrictive. The scope of the present invention is defined by the attached claims rather than by the embodiments, and all changes equivalent to the configurations of claims are enclosed therein.

For example, in the embodiment, the reflected light is detected by the outer end surface of the light reflecting unit 103 having a bar shape embedded in the rotor 72, but the rotation information can also be acquired by forming a pass-through hole in the peripheral surface of the rotor 72 and detecting the light emitted from the light emitting unit 101 by the light receiving unit 102 via the pass-through hole of the rotor 72 during rotation. In this case, the light emitting unit 101 and the light receiving unit 102 are arranged in a position facing each other with the rotor 72 in between.

In the embodiments, a member having a bar shape is used as the light reflecting unit, but a member in which a metal having a sheet or film shape is adhered to the peripheral surface of the rotor 72 can also be used as the light reflecting unit.

In the embodiments, the rotor 72 rotating is irradiated with light and the reflected light from the rotor 72 is detected, but the rotation information of the rotor 72 can also be acquired by providing a light-emitting element in the rotor 72 itself and detecting the light from the light-emitting element.

In the embodiments, the rotation information of the rotor 72 is acquired using light, but the information related to the rotational state of the rotor 72 can also be acquired by detecting a flow of the liquid sample in the substitution container generated by rotating the rotor 72.

The information related to the rotation of the rotor 72 can also be acquired using ultrasonic waves or radars.

The information related to the rotation of the rotor 72 can also be acquired by detecting a magnetic field generated by the rotation of the rotor 72 with a magnetic sensor.

In addition to the capacitance type sensor, a photoelectric sensor and an ultrasonic sensor can be appropriately employed as a liquid surface detecting means for detecting the surface of the liquid in the substitution container 57. In the case of the photoelectric sensor, the surface of the liquid in the substitution container 57 can be detected without allowing a sensor unit to project to the substitution container 57.

In the embodiments, the epithelial cells of the uterine cervix are used as the cells to be measured, but the malignant transformation of buccal cells, epithelial cells of the bladder and the pharynx, and epithelial cells of organs can be determined.

In the embodiments, the liquid sample is separated into the first liquid and the second liquid by applying the negative pressure to the piston 58 so as to move the piston 58 to the lower side following the lowering of the surface of the first liquid, but the liquid sample may be separated into the first liquid and the second liquid by sealing between the upper opening portion in the substitution container 57 and the piston 58 to which the filter 60 is fixed with a sealing member and moving the piston 58 to the lower side by the driving unit 59. The cells to be measured contained in the first liquid held in the holding chamber 68 are moved to the condensed sample holding chamber 80 by rotating the rotor 72, and then the liquid sample present in the condensed sample holding chamber 80 may be obtained. Thus, only cells, such as red blood cells and white blood cells, except the epithelial cells which are the cells to be measured pass the filter 60, while the epithelial cells which are the cells to be measured do not pass the filter 60 and are held in the holding chamber 68. Thus, the liquid in which the number of cells other than the cells to be measured is reduced can be obtained.

In the embodiments, the measurement sample prepared by the sample preparation apparatus 3 is measured by the flow cytometer, but a smeared specimen preparing apparatus which smears the measurement sample prepared by the sample preparation apparatus 3 on a slide glass to prepare a smeared specimen and a cell image processing apparatus which images the smeared specimen prepared and analyzes epithelial cells in the imaged image may be provided. Since the measurement sample in which the concentration of the epithelial cells which are the cells to be measured is increased and the number of cells, such as red blood cells and white blood cells, is reduced is smeared on the slide glass, the epithelial cells can be analyzed with sufficient accuracy.

In the embodiments, the rotor 72 is rotated after applying pressure from the upper side of the filter 60 to the through holes of the filter 60, but the pressure may be applied from the upper side of the filter 60 to the through holes of the filter 60 after rotating the rotor 72. In the embodiments, the rotor 72 is rotated while applying pressure to the through holes of the filter 60, but the rotor 72 may be rotated after completion of applying pressure to the through holes of the filter 60.

In the embodiments, the control of the drive voltage to the driving motor 70a is performed at the time of activating the apparatus, but the present invention is not limited thereto, the control of the drive voltage to the driving motor 70a may be performed based on the rotating speed acquired by the monitoring of the rotation in checking at the time of measurement (retry process) and after the measurement (adhesion-preventive process).

What is claimed is:

1. A sample preparation apparatus comprising:
   a filter comprising a plurality of holes having a first diameter configured to separate predetermined cells having a second diameter larger than the first diameter from a liquid sample containing a plurality of types of cells, the predetermined cells being trapped on a surface of the filter;
   a rotor which includes a magnetic body, the rotor being provided to face to the surface of the filter;
   a driving unit which is configured to rotate the rotor using a magnetic force;
   a rotation information acquiring unit which is configured to acquire rotation information of the rotor when the driving unit rotates the rotor;
   a holding chamber sidewall defining a holding chamber which is configured to hold the rotor and an opening along an outer circumference of the holding chamber; and
   a condensed sample holding chamber attached to the holding chamber at the opening such that the condensed sample holding chamber is disposed adjacent to the outer circumference of the sidewall of the holding chamber,
   wherein the rotor is configured to move the predetermined cells from the holding chamber to the condensed sample holding chamber.

2. The apparatus of claim 1, wherein
   the rotation information acquiring unit includes a light emitting unit which irradiates the rotor with light and a light receiving unit which detects the light emitted from the light emitting unit
   and acquires the rotation information based on a light information detected by the light receiving unit.

3. The apparatus of claim 2, wherein
   the rotor includes a light reflecting unit which reflects the light
   and the light receiving unit detects light from the light emitting unit reflected by the light reflecting unit during rotation of the rotor.

4. The apparatus of claim 3, wherein
   the rotor has a circular cylindrical shape
   and the light reflecting unit is embedded in a concave portion formed in the peripheral surface of the rotor.

5. The apparatus of claim 1, wherein
   the rotation information acquiring unit acquires a rotating speed of the rotor per a predetermined time as the rotation information.

6. The apparatus of claim 1, wherein
the driving unit is controlled based on the rotation information of the rotor acquired by the rotation information acquiring unit.

7. The apparatus of claim 6, wherein
a driving force of the driving unit is increased when the rotating speed of the rotor is lower than a predetermined threshold.

8. The apparatus of claim 6, wherein
a driving force of the driving unit is decreased when the rotating speed of the rotor is higher than a predetermined threshold.

9. The apparatus of claim 1, wherein
the acquired rotation information of the rotor is the rotating speed of the rotor per the predetermined time
and the driving unit is controlled so that the rotating speed of the rotor is within a predetermined rotating speed range.

10. The apparatus of claim 1, further comprising
a control unit which controls the driving unit based on the rotation information of the rotor acquired by the rotation information acquiring unit.

11. The apparatus of claim 1, wherein
the driving unit includes a driving magnetic body which attaches the rotor with the magnetic force and a driving source which rotates the driving magnetic body.

12. The apparatus of claim 1, further comprising:
a cell obtaining unit which obtains the predetermined cells detached by the rotor; and
a sample preparation unit which prepares a measurement sample from the predetermined cells obtained by the cell obtaining unit and a predetermined reagent.

13. The apparatus of claim 12, wherein
the rotation information acquiring unit rotates the rotor to acquire the rotation information of the rotor at the time of completing measurement using the prepared measurement sample.

14. The apparatus of claim 1, further comprising
a cleaning unit which cleans the rotor.

15. The apparatus of claim 13, wherein
the acquired rotation information of the rotor is the rotating speed of the rotor per the predetermined time, and
the cleaning unit starts cleaning of the rotor when the rotating speed of the rotor is lower than the predetermined threshold.

16. The apparatus of claim 1, wherein
the rotation information acquiring unit rotates the rotor to acquire the rotation information of the rotor at the time of activating the apparatus.

17. The apparatus of claim 1, wherein
the rotation information acquiring unit acquires the rotation information of the rotor at the time of detaching the predetermined cells by the rotor.

18. The apparatus of claim 1, wherein
the filter separates cells of uterine cervix as the predetermined cells from a liquid sample containing a plurality types of cells.

19. The apparatus of claim 1, wherein the condensed sample holding chamber is arranged in a periphery part of the holding chamber.

* * * * *